United States Patent
Ano et al.

(10) Patent No.: US 12,019,043 B2
(45) Date of Patent: Jun. 25, 2024

(54) IMPEDANCE MEASUREMENT

(71) Applicant: Analog Devices International Unlimited Company, Limerick (IE)

(72) Inventors: Jose Carlos Conchell Ano, Valencia (ES); Javier Calpe Maravilla, Algemesi (ES); Liam Patrick Riordan, Patrickswell (IE)

(73) Assignee: Analog Devices International Unlimited Company, Limerick (IE)

( * ) Notice: Subject to any disclaimer, the term of this patent is extended or adjusted under 35 U.S.C. 154(b) by 0 days.

(21) Appl. No.: 17/360,873

(22) Filed: Jun. 28, 2021

(65) Prior Publication Data
US 2021/0325328 A1   Oct. 21, 2021

Related U.S. Application Data

(63) Continuation of application No. 16/374,021, filed on Apr. 3, 2019, now Pat. No. 11,047,821.
(Continued)

(51) Int. Cl.
*G01R 27/08* (2006.01)
*A61B 5/0531* (2021.01)
(Continued)

(52) U.S. Cl.
CPC ......... *G01N 27/028* (2013.01); *A61B 5/0531* (2013.01); *A61B 5/0537* (2013.01);
(Continued)

(58) Field of Classification Search
CPC .. G01N 27/028; A61B 5/0531; A61B 5/0537; A61B 5/0809; A61B 5/053;
(Continued)

(56) References Cited

U.S. PATENT DOCUMENTS

| 4,917,099 A | 4/1990 | Stice |
| 5,020,541 A | 6/1991 | Marriott |

(Continued)

FOREIGN PATENT DOCUMENTS

| CN | 101194834 A | 6/2008 |
| CN | 101999899 A | 4/2011 |

(Continued)

OTHER PUBLICATIONS

BERA, Tushar Kanti, "Bioelectrical Impedance and The Frequency Dependent Current Conduction Through Biological Tissues: A Short Review," 3rd International Conference on Communication Systems (ICCS-2017), 10 pages.

(Continued)

*Primary Examiner* — Raul J Rios Russo
(74) *Attorney, Agent, or Firm* — ARENTFOX SCHIFF LLP

(57) ABSTRACT

Accurately measuring bio-impedance is important for sensing properties of the body. Unfortunately, contact impedances can significantly degrade the accuracy of bio-impedance measurements. To address this issue, circuitry for implementing a four-wire impedance measurement can be configured to make multiple current measurements. The multiple current measurements set up a system of equations to allow the unknown bio-impedance and contact impedances to be derived. The result is an accurate bio-impedance measurement that is not negatively impacted by large contact impedances. Moreover, bad contacts with undesirably large impedances can be identified.

20 Claims, 16 Drawing Sheets

Related U.S. Application Data

(60) Provisional application No. 62/679,460, filed on Jun. 1, 2018, provisional application No. 62/678,986, filed on May 31, 2018.

(51) Int. Cl.

| | | |
|---|---|---|
| *A61B 5/0537* | (2021.01) | |
| *A61B 5/08* | (2006.01) | |
| *G01N 27/02* | (2006.01) | |
| *G01R 1/20* | (2006.01) | |
| *G01R 19/00* | (2006.01) | |
| *G01R 27/02* | (2006.01) | |
| *G01R 27/14* | (2006.01) | |

(52) U.S. Cl.
 CPC ............ *A61B 5/0809* (2013.01); *G01R 1/203* (2013.01); *G01R 19/0092* (2013.01); *G01R 27/02* (2013.01); *G01R 27/08* (2013.01); *G01R 27/14* (2013.01); *H01L 2224/48091* (2013.01); *H01L 2224/48472* (2013.01); *H01L 2924/00* (2013.01)

(58) Field of Classification Search
 CPC .... A61B 5/0536; A61B 5/7225; G01R 1/203; G01R 19/0092; G01R 27/08; G01R 27/14; G01R 27/02; G01R 27/16; H01L 2224/48091; H01L 2224/48472; H01L 2924/00
 USPC .......... 324/76.11–76.83, 439, 459, 522, 549, 324/649, 691, 713
 See application file for complete search history.

(56) References Cited

U.S. PATENT DOCUMENTS

| | | | |
|---|---|---|---|
| 6,007,532 A | 12/1999 | Netherly | |
| 6,567,692 B1 | 5/2003 | Kohashi et al. | |
| 9,351,653 B1 | 5/2016 | Harrison | |
| 2003/0216661 A1 | 11/2003 | Davies | |
| 2004/0158167 A1 | 8/2004 | Smith et al. | |
| 2006/0064029 A1 | 3/2006 | Arad | |
| 2007/0010758 A1* | 1/2007 | Matthiessen | H03F 3/45475 600/425 |
| 2007/0194776 A1 | 8/2007 | Bossche | |
| 2008/0275316 A1 | 11/2008 | Fink et al. | |
| 2008/0294358 A1* | 11/2008 | Richardson | G01R 27/02 702/57 |
| 2009/0247898 A1 | 10/2009 | Robitzki et al. | |
| 2009/0326600 A1 | 12/2009 | Kracker | |
| 2010/0004548 A1 | 1/2010 | Rytky | |
| 2010/0168530 A1 | 7/2010 | Chetham et al. | |
| 2011/0074442 A1* | 3/2011 | Min | A61B 5/053 324/647 |
| 2011/0204971 A1 | 8/2011 | Chang et al. | |
| 2011/0208458 A1* | 8/2011 | Pinter | A61B 5/053 702/65 |
| 2011/0237904 A1 | 9/2011 | Kim | |
| 2011/0251817 A1 | 10/2011 | Burns et al. | |
| 2013/0102920 A1 | 4/2013 | Fan et al. | |
| 2014/0257119 A1 | 9/2014 | LeMay | |
| 2014/0296662 A1 | 10/2014 | Hayn et al. | |
| 2015/0119747 A1 | 4/2015 | Torfs et al. | |
| 2015/0293045 A1* | 10/2015 | Udupa | A61B 5/6898 324/692 |
| 2016/0015290 A1 | 1/2016 | Kim et al. | |
| 2016/0106337 A1 | 4/2016 | Jung et al. | |
| 2016/0195484 A1 | 7/2016 | Emery | |
| 2016/0344352 A1 | 11/2016 | Chang et al. | |
| 2017/0071552 A1 | 3/2017 | Harpe et al. | |
| 2017/0191980 A1 | 7/2017 | Robitzki et al. | |
| 2017/0219509 A1 | 8/2017 | Bakalos et al. | |
| 2018/0116545 A1 | 5/2018 | Hwang et al. | |
| 2018/0140226 A1 | 5/2018 | Mathiasmeier et al. | |
| 2019/0059777 A1* | 2/2019 | Aga | A61B 5/7203 |
| 2019/0137566 A1 | 5/2019 | Ormston | |
| 2019/0212284 A1 | 7/2019 | Emery | |
| 2020/0096463 A1* | 3/2020 | Ano | A61B 5/053 |
| 2020/0163577 A1* | 5/2020 | Chen | A61B 5/7203 |
| 2021/0401317 A1* | 12/2021 | Chételat | G01R 29/12 |

FOREIGN PATENT DOCUMENTS

| | | | | |
|---|---|---|---|---|
| CN | 102973267 | A | 3/2013 | |
| CN | 103930021 | A | 7/2014 | |
| CN | 105559781 | A | 5/2016 | |
| CN | 205215226 | U | 5/2016 | |
| CN | 106618569 | A | 5/2017 | |
| EP | 3153099 | | * 7/2016 | ............ A61B 5/053 |
| IN | 105656489 | A | 6/2016 | |
| JP | H1170090 | A | 3/1999 | |
| JP | 2001187029 | A | 7/2001 | |
| JP | 2003062034 | A | 3/2003 | |
| JP | 2015002779 | A | 1/2015 | |
| KR | 20110019773 | A | 2/2011 | |
| WO | 2014021883 | A1 | 2/2014 | |

OTHER PUBLICATIONS

Broeders, Jan-Hein, "Wearable Electronic Devices Monitor Vital Signs , Activity Level , and More Health Monitoring Is Going Wearable," Analogue Dialogue, 48-12, Dec. 2014, 6 pages.

Demidenko, Eugene, "An analytic solution to the homogeneous EIT problem on the 2D disk and its application to estimation of electrode contact impedances," NIH Public Access, Author Manuscript, Physiol Meas., Sep. 2011, vol. 32, No. 9, 24 pages.

Extended European Search Report in EP1917528.5, mailed Ot. 9, 2019, 8 pages.

International Search Report and Written Opinion in PCT/EP2020/050545, mailed Mar. 31, 2020, 13 pages.

Office Action in CN201910465785.2, mailed Dec. 2, 2022, 7 pages.

Chang et al., "Research and Applications of Electrical Bioimpedance Measurement Technology," Chinese Journal of Medical Physics, Mar. 2015, vol. 32, No. 2, 5 pages.

Office Action in CN201910465785.2, ,mailed Jun. 8 2023, 8 pages.

* cited by examiner

US 12,019,043 B2

IMPEDANCE MEASUREMENT

PRIORITY APPLICATIONS

This continuation patent application claims priority to and receives benefit from U.S. Non-Provisional application Ser. No. 16/374,021, titled "BIO-IMPEDANCE AND CONTACT IMPEDANCES MEASUREMENT", filed on Apr. 3, 2019. The US Non-Provisional Application claims priority to and receives benefit from U.S. Provisional Application Ser. No. 62/678,986, titled "BIO-IMPEDANCE AND CONTACT IMPEDANCES MEASUREMENT", filed on May 31, 2018, and U.S. Provisional Application Ser. No. 62/679,460, titled "BIO-IMPEDANCE AND CONTACT IMPEDANCES MEASUREMENT", filed on Jun. 1, 2018. The US Non-Provisional Application and the two US Provisional Applications are hereby incorporated in their entirety.

TECHNICAL FIELD OF THE DISCLOSURE

The present invention relates to the field of integrated circuits, in particular to impedance measurements.

BACKGROUND

Impedance measurements of the body, referred herein as bio-impedance, has many applications in healthcare and consumer applications. Impedance measurements can be made by electrodes provided in body-worn systems, or wearable devices, such as wrist watches, chest bands, head bands, patches, and so on. Circuitry coupled to the electrodes can derive the unknown impedance of the body on which the electrodes are placed. Impedance measurements can be particularly useful for vital-signs monitoring, sensing of tissues and fluid level in the body for purposes of detecting signs of pulmonary edema, or assess body composition. Moreover, electrical impedance tomography is an emerging non-invasive technique of medical imaging. Due to various challenges, making an accurate bio-impedance measurement is not trivial.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DESCRIPTION OF EXAMPLE EMBODIMENTS OF THE DISCLOSURE

Overview

Accurately measuring bio-impedance is important for sensing properties of the body. Unfortunately, contact impedances can significantly degrade the accuracy of bio-impedance measurements. To address this issue, circuitry for implementing a four-wire impedance measurement can be configured to make multiple current measurements. The multiple current measurements set up a system of equations to allow the unknown bio-impedance and contact impedances to be derived. The result is an accurate bio-impedance measurement that is not negatively impacted by large contact impedances. Moreover, bad contacts with undesirably large impedances can be identified.

Four-Wire Impedance Measurement

One technique for impedance measurement is a four-terminal sensing scheme, or four-wire impedance measurement scheme. Sometimes it is referred to as Kelvin sensing. The technique involves using four electrodes placed on the body to sense or derive an unknown bio-impedance.

Figure 1:
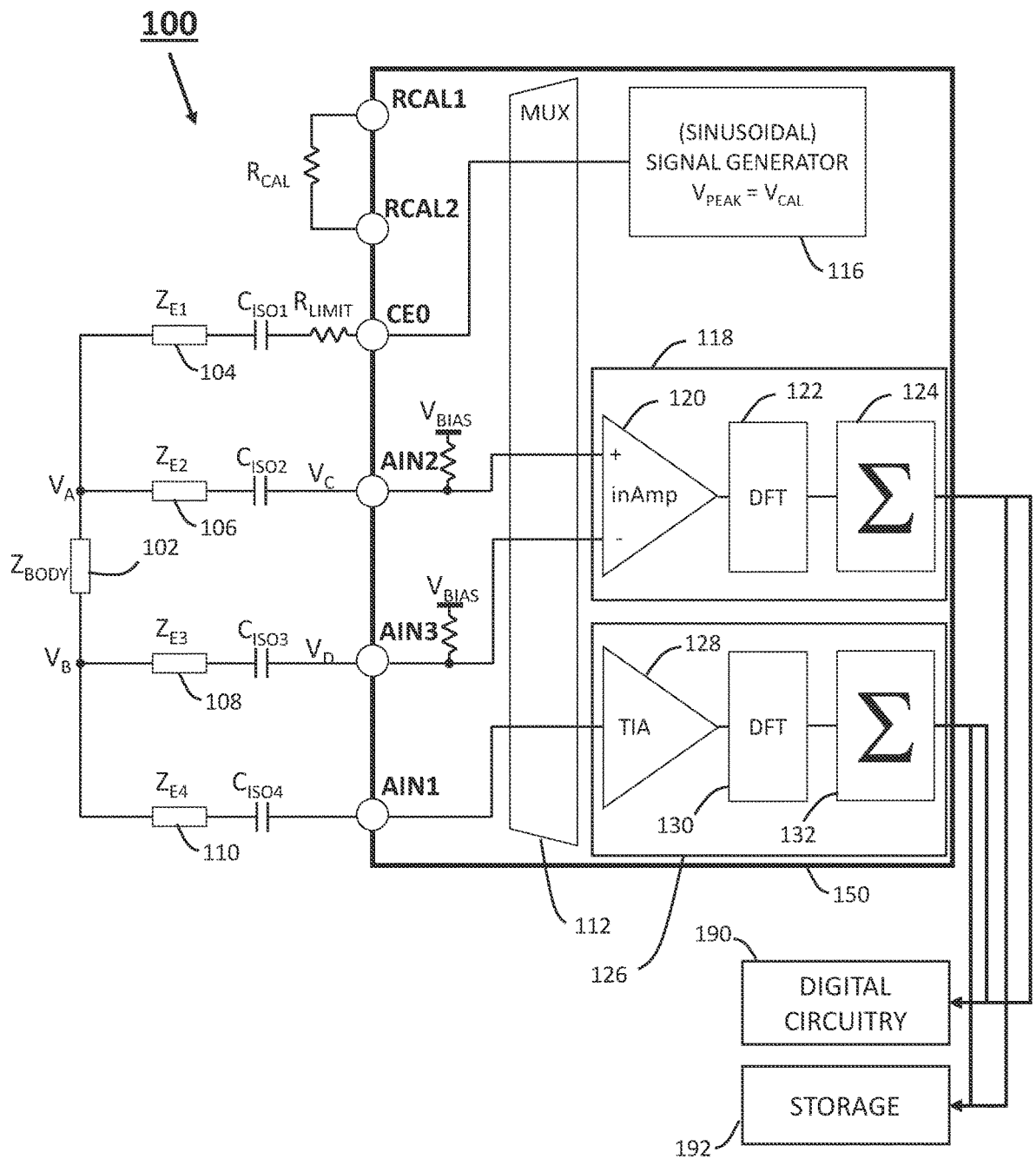
FIG. 1 illustrates a system having electrodes and circuitry for performing one exemplary way of making a four-wire impedance measurement of bio-impedance, according to some embodiments of the disclosure.

FIG. 1 illustrates a system 100 having electrodes and circuitry for performing one exemplary way making a four-wire impedance measurement of bio-impedance, according to some embodiments of the disclosure. In the FIGURE, the unknown bio-impedance is shown as $Z_{BODY}$. The system 100 includes electrodes 104, 106, 108, and 110 (or contacts to the body). The electrodes 104, 106, 108, and 110 have respective contact impedances $Z_{E1}$, $Z_{E2}$, $Z_{E3}$, and $Z_{E4}$. Contact impedances $Z_{E1}$, $Z_{E2}$, $Z_{E3}$, and $Z_{E4}$ can represent skin-electrode impedance of the electrodes 104, 106, 108, and 110, respectively. Circuitry 150, packaged as an integrated circuit or chip, has pins (or connections) to which the electrodes are connected. Pin CE0 is electrically coupled to electrode 104. Pin AIN2 is electrically coupled to electrode 106. Pin AIN3 is electrically coupled to electrode 108. Pin AIN1 is electrically coupled to electrode 110.

The system 100 has four branches: a branch that includes electrode 104 and pin CE0, a branch that includes electrode 106 and pin AIN2, a branch that includes electrode 108 and pin AIN3, and a branch that includes electrode 110 and pin AIN1. Two branches are for sensing a first end of the unknown bio-impedance $Z_{BODY}$, and two other branches are for sensing a second end of the unknown bio-impedance $Z_{BODY}$. The branch that includes electrode 104 is coupled to the first end of unknown bio-impedance $Z_{BODY}$. The branch that includes electrode 106 is coupled to the first end of unknown bio-impedance $Z_{BODY}$. The branch that includes electrode 108 is coupled to the second end of unknown bio-impedance $Z_{BODY}$. The branch that includes electrode 110 is coupled to the second end of unknown bio-impedance $Z_{BODY}$. The four branches are connected to respective pins of circuitry 150. Parts of the branches outside of circuitry 150 can represent cables with patches at the end of the cables. Parts of the branches outside of circuitry 150 can also represent conductors or wires having electrodes at the end of the conductors or wires. The conductors and electrodes can be fitted in a wearable device. Optionally, capacitances shown $C_{ISO1}$, $C_{ISO2}$, $C_{ISO3}$, $C_{ISO4}$ can be included between respective pairs of electrodes and pins to provide isolation and protection between the body of the human user and the circuitry within circuitry 150 (e.g., to block DC signals).

Circuitry 150 can include a multiplexer (mux) 112. Mux 112 can be controlled in a manner to connect signal paths of the different pins to different parts of circuitry 150. Mux 112, as used herein, represents a configurable network controllable to connect different parts of circuitry 150 to different pins. For instance, mux 112 can connect different parts of circuitry 150 to different branches connected to the pins (the branches having respective electrodes). Different configurations of mux 112 can form different signal paths or different impedance networks (impedance networks being synonymous with signal paths).

Circuitry 150 can include a signal generator 116 (e.g., sinusoidal signal generator). Signal generator can generate a signal having a peak voltage of $V_{PEAK}$. The signal generator generates the signal at an output of the signal generator.

Circuitry 150 can include voltage measurement circuitry 118 to measure a voltage across a positive input and a negative input of the voltage measurement circuitry 118. In some embodiments, voltage measurement circuitry 118 can include an instrumentation amplifier (inAmp) 120 with a positive terminal and a negative terminal to sense a voltage difference between the positive terminal and negative terminal, and outputs a voltage output representative of that voltage difference. Voltage measurement circuitry 118 can include a Discrete Fourier Transform (DFT) block 122 and summation block 124 to generate a voltage measurement based on the voltage output from inAmp 120. Components for generating a voltage measurement (e.g., a difference in voltage between two inputs) can differ depending on the implementation.

Circuitry 150 can further include current measurement circuitry 126 to measure a current at an input of the current measurement circuitry 126. In some embodiments, current measurement circuitry 126 can include a transimpedance amplifier (TIA) 128 to convert a current at an input terminal of the TIA 128 to a voltage output representative of the current. Current measurement circuitry 126 can include a DFT block 130 and summation block 132 to generate a current measurement based on the voltage output from TIA 128. Components for generating a current measurement (e.g., an amount of current flowing through an input) can differ depending on the implementation.

To make an impedance measurement, a voltage is generated across the unknown bio-impedance shown as $Z_{BODY}$. The voltage across the unknown bio-impedance $Z_{BODY}$ can be viewed as $V_A$-$V_B$. The voltage across the unknown bio-impedance $Z_{BODY}$ can be generated or imposed by signal generator 116. Meanwhile, the voltage across the unknown bio-impedance $Z_{BODY}$ is measured by the voltage measurement circuitry 118, and the current through the unknown bio-impedance $Z_{BODY}$ is also measured, by current measurement circuitry 126. The measured voltage and the measured current can be used to derive the impedance value of the unknown bio-impedance $Z_{BODY}$. Specifically, the impedance value of the unknown bio-impedance $Z_{BODY}$ is related to the voltage measurement divided by the current measurement.

In conventional two-wire impedance measurements, measurement issues can arise from impedances of cables (including contact impedances) being added to the unknown bio-impedance $Z_{BODY}$, thus corrupting the impedance measurement. For simplicity, the impedances present are lumped together as a contact impedance in each branch. In theory, a four-wire impedance measurement can avoid such issues.

When the unknown bio-impedance $Z_{BODY}$ is much higher than the impedances of the cables, the measurements can be sufficiently accurate.

However, in practice, a four-wire impedance measurement can have certain other limitations or non-idealities that can significantly impact the accuracy of the bio-impedance measurement. These limitations can be significant, e.g., when making impedance measurements at low frequencies, high frequencies, certain frequencies, or various frequencies. In some situations, one or more of the contact impedances $Z_{E1}$, $Z_{E2}$, $Z_{E3}$, and $Z_{E4}$ can be greater than the unknown bio-impedance $Z_{BODY}$. For instance, mechanical and/or environmental reasons (e.g., humidity, movement, hair on skin, etc.) can cause poor contacts, and can severely increase one or more of the contact impedances. In some severe cases, the (magnitude of) contact impedances can be greater than 2 kΩ. In some situations, the optional capacitors $C_{ISO1}$, $C_{ISO2}$, $C_{ISO3}$, $C_{ISO4}$ can also significantly increase or affect the impedances of the cables. In some situations, the contact impedances $Z_{E1}$, $Z_{E2}$, $Z_{E3}$, and $Z_{E4}$ can have an imbalance with each other (e.g., imbalance can be greater than 1 kΩ). These limitations have been found to degrade the accuracy of the four-wire impedance measurement.

Figure 2:
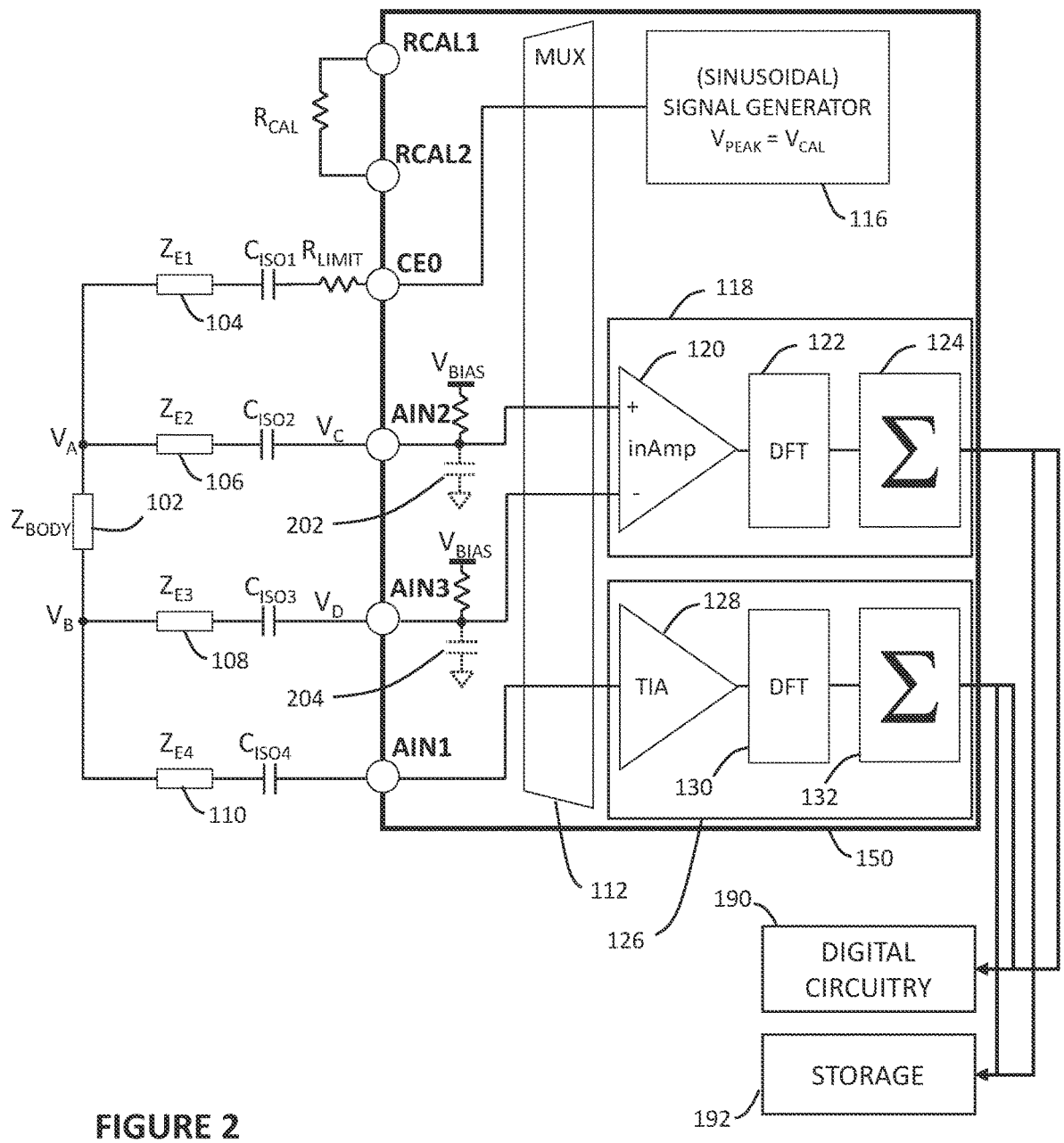
FIG. 2 illustrates input capacitances present in circuitry that performs a four-wire impedance measurement of bio-impedance, according to some embodiments of the disclosure.

One of the problems causing these limitations that degrade the accuracy of the bio-impedance measurement is that there can be large input capacitances at pin AIN2 and pin AIN3 (e.g., around 40 pF). FIG. 2 illustrates input capacitances present in circuitry that performs a four-wire impedance measurement of bio-impedance, according to some embodiments of the disclosure. Grounded input capacitance 202 can be present at pin AIN2, and grounded input capacitance 204 can also be present at pin AIN3. Grounded input capacitance 202, contact impedance $Z_{E2}$, and capacitance $C_{ISO2}$ can form a filter. This filter can be problematic because the contact impedance $Z_{E2}$ is unknown, and thus the effect of the filter is unknown as well. Grounded input capacitance 204, contact impedance $Z_{E3}$, and capacitance $C_{ISO3}$ can also form another filter. This other filter can be problematic because the contact impedance $Z_{E3}$ is unknown, and thus the effect of this other filter is unknown as well. Ideally, voltage $V_A$ should be the same as the voltage $V_C$, and voltage $V_B$ should be the same as the voltage $V_D$. Due to the grounded input capacitances 202 and 204, at certain frequencies, voltage $V_A$ is not the same as the voltage $V_C$, and voltage $V_B$ is not the same as the voltage $V_D$. The voltage across $V_A$ and $V_B$ may not be the same as the voltage across $V_C$ and $V_D$. The negative effect of the grounded input capacitances 202 and 204 can be observable at low frequencies and when contact impedances are high, e.g., in the range of hundreds or thousands of Ohms. Furthermore, the grounded input capacitances 202 and 204 can attribute to imbalances in the contact impedances. Imbalances in the contact impedances of the branches can produce different cut-off frequencies, thereby causing different attenuations in each branch.

Figure 3:
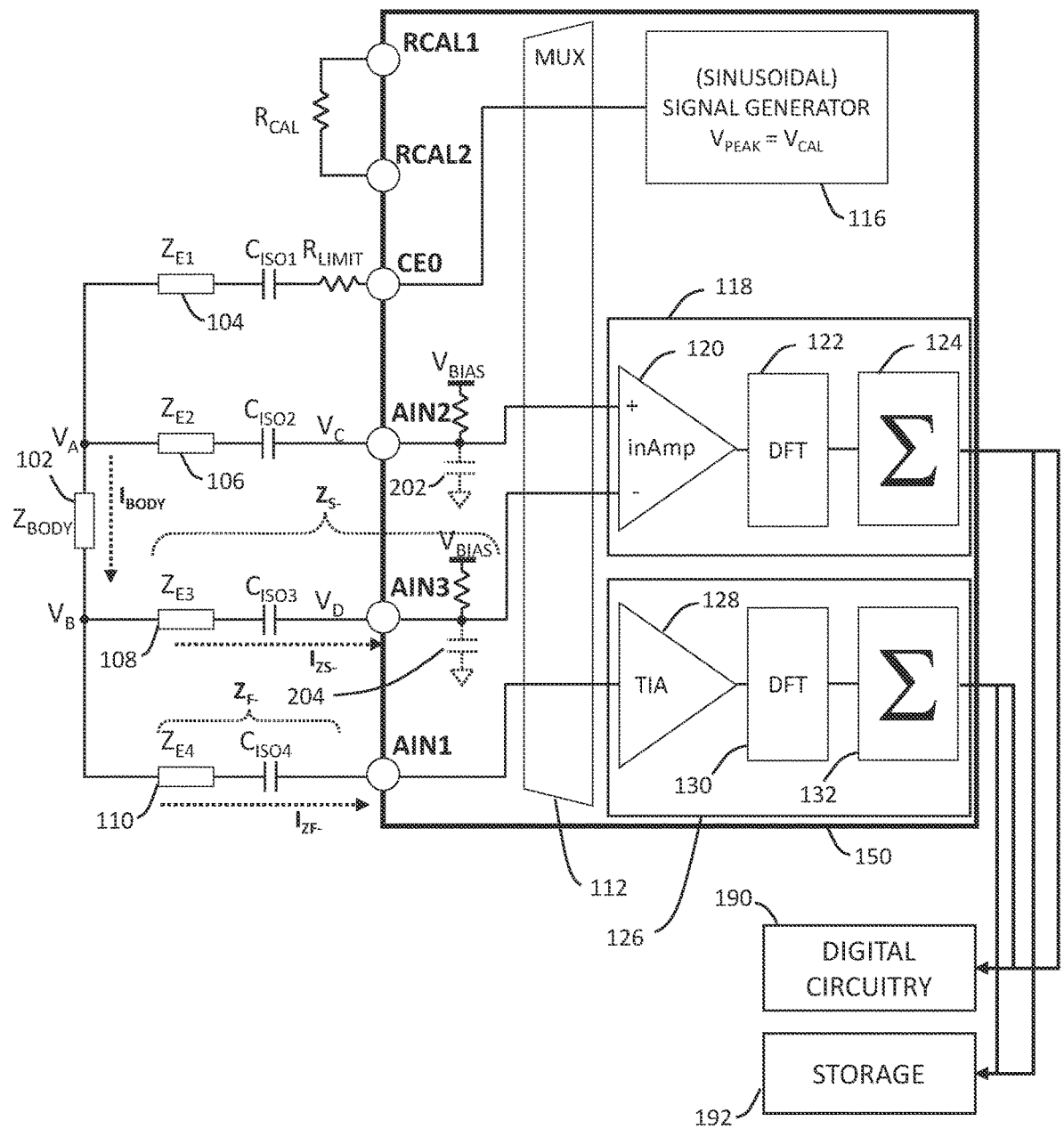
FIG. 3 illustrates current leakage present in circuitry that performs a four-wire impedance measurement of bio-impedance, according to some embodiments of the disclosure.

Another problem that may degrade the accuracy of the bio-impedance measurement is current leakage. FIG. 3 illustrates current leakage present in circuitry that performs a four-wire impedance measurement of bio-impedance, according to some embodiments of the disclosure. The current leakage arises because the impedance $Z_{S-}$ of the branch having electrode 108 can be similar to the impedance $Z_{F-}$ of the branch having electrode 110 driving the TIA 128. This results in some of the current $I_{BODY}$ flowing through the unknown bio-impedance $Z_{BODY}$ to flow through the branch having electrode 108, and not all of the current $I_{BODY}$ would flow through the branch having electrode 110. In other words, the current $I_{ZS}$ through the branch having electrode 108 is ideally zero, and the current $I_{ZF}$ through the branch having electrode 110 is ideally equal to current $I_{BODY}$. In reality, the current $I_{ZS}$ is not zero. As a result, the current $I_{ZF}$ through the branch having electrode 110 is not equal to current $I_{BODY}$, and part of current $I_{BODY}$ is not measured by the current measurement circuitry 126. The current measurement is corrupted, and thus the impedance measurement is also corrupted. This issue can be exacerbated by high contact impedances in the branches.

An Exemplary Scheme for Deriving Contact Impedances Through Multiple Measurements and Signal Processing By configuring mux 112 and making multiple current measurements, it is possible to derive the (unknown) impedances of the system, including the unknown bio-impedance $Z_{BODY}$, and the contact impedances $Z_{E1}$, $Z_{E2}$, $Z_{E3}$, and $Z_{E4}$, based on a system of equations. The system of equations are formed through a calibration measurement, and several other current measurements of different signal paths formed by configuring mux 112. Mux 112 can selectively couple the output of the signal generator 116 and the input of the current measurement circuitry 126 to different pins (e.g., RCAL1, RCAL2, CE0, AIN2, AIN3, and AIN1). Accordingly, mux 112 can connect the output of the signal generator 116 to the input of the current measurement circuitry 126 through different signal paths, or different impedance networks involving at least some of the unknown impedances. The different signal paths, individually, can include two or more of the unknown impedances of the system: the unknown bio-impedance $Z_{BODY}$, and the contact impedances $Z_{E1}$, $Z_{E2}$, $Z_{E3}$, and $Z_{E4}$. Unique signal paths or unique impedance networks of at least some of the unknown impedances, and the current measurements of the unique signal paths or unique impedance networks, setup a system of equations for the unknown impedances. The unique signal paths or unique impedance networks, together, include each one of the unknown impedances at least once. Each unique signal path or unique impedance network would include at least some of the unknown impedances of the system. Effectively, the signal generator 116 can excite unique signal paths or unique impedance networks formed by mux 112, and the current measurement circuitry 126 can make measurements of current going through the unique signal paths or unique impedance networks.

To determine five unknown impedances (the bio-impedance and the four contact impedances), at least five equations are needed. With a sufficient number of equations, it is possible to derive the five unknown impedances through signal processing (i.e., calculations). Through suitable processing, the current measurements allow the bio-impedance and the contact impedances to be determined. The current measurements can be performed by the current measurement circuitry 126. The signal processing can be performed in the digital domain, e.g., by digital circuitry 190. Digital circuitry 190 can include specialized digital hardware to perform the signal processing. Digital circuitry 190 can include a microprocessor or microcontroller configured to carry out instructions that implement the signal processing. The digital circuitry 190 can be provided on-chip with circuitry 150 or off-chip (as shown). Digital circuitry 190 can be implemented to control mux 112 to form unique signal paths or unique impedance networks from the signal generator 116 to the current measurement circuitry 126. Computer-readable storage 192 can store the measurements. Computer-readable storage 192 can store the instructions that implement the signal processing. The computer-readable storage 192 can be provided on-chip with circuitry 150 or off-chip (as shown).

Figure 4:
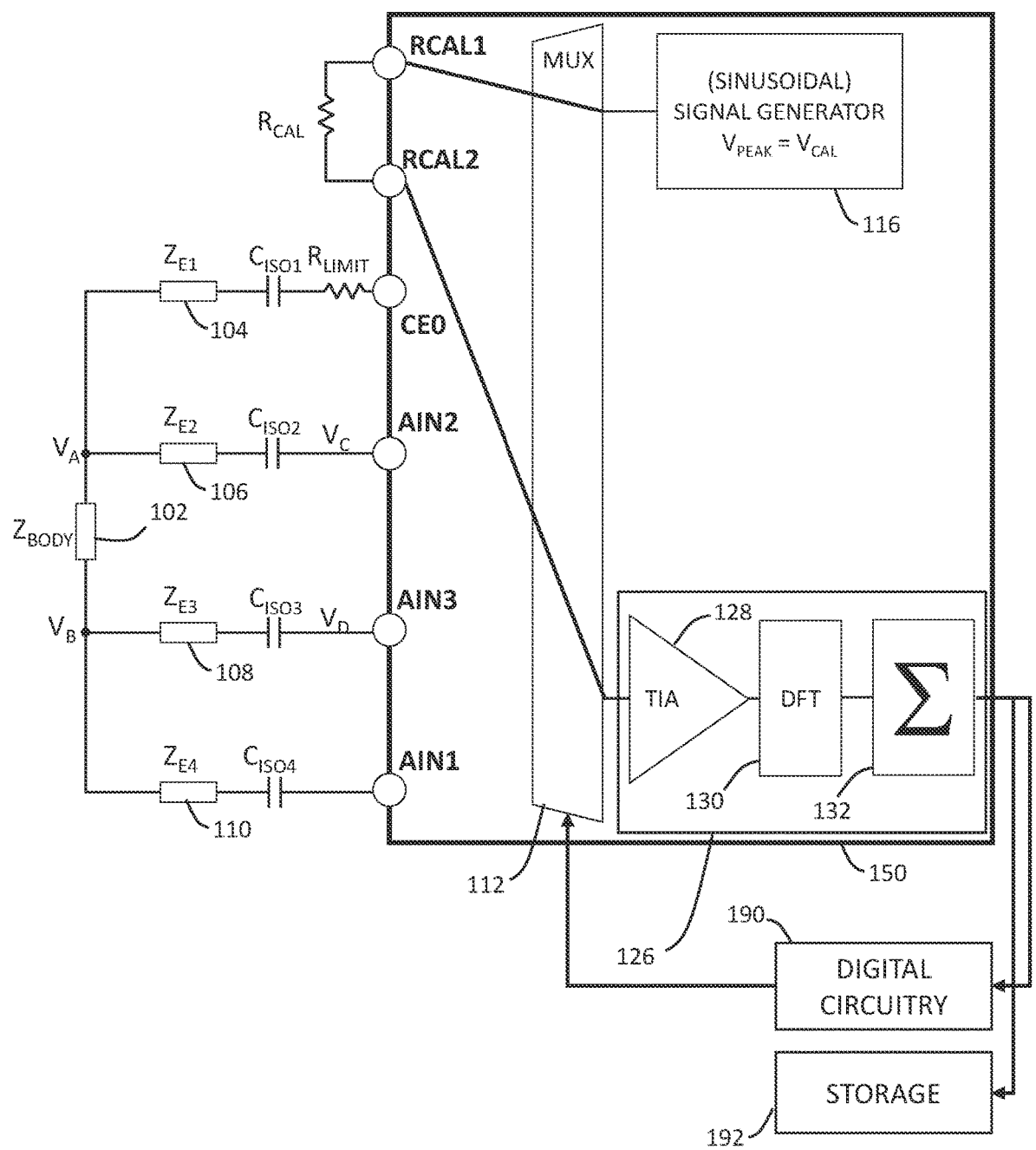
FIG. 4 illustrates a calibration measurement, according to some embodiments of the disclosure.

FIG. 4 illustrates a calibration measurement, according to some embodiments of the disclosure. The calibration measurement is performed to determine a peak voltage from the signal generator 116, if it is not already measured or if it is not already known. The system of equations (shown as equations 2-6 below) being formed by the current measurements of unique signal paths going through at least some of the unknown impedances use the peak voltage measured in the calibration measurement as a numerical constant. The unknown impedances would be derived based further on the peak voltage measured in the calibration measurement. Determining the peak voltage from the signal generator 116 can be performed in various ways. An output from the signal generator 116 can be applied to a resistor with a known resistance value, and the current measurement circuitry 126 can measure a current through the resistor. The calibration measurement is represented by: $V_{CAL}=I_{CAL} \cdot R_{CAL}$ (reproduced as equation 1 below). $R_{CAL}$ is a resistor with a known stable resistance value. $I_{CAL}$ is measured by the current measurement circuitry 126. Accordingly, $V_{CAL}$, which is the voltage from signal generator 116 can be derived.

The resistor with a known resistance value can be provided on-chip with circuitry 150 or off-chip (as shown). The calibration measurement is optional if the peak voltage from the signal generator is known. The calibration measurement may only need to be performed once, and does not need to be performed every time impedance measurements are being made.

In the example shown, for the calibration measurement, an (off-chip) resistor $R_{CAL}$ having a known, stable resistance value is coupled across pins RCAL1 and RCAL2. The mux 112 is configured to couple the signal path from pin RCAL1 to the signal generator 116 and to couple the signal path from pin RCAL2 to the current measurement circuitry 126. The mux 112 forms a signal path from the output of signal generator 116 to input of current measurement circuitry 126, and the signal path includes resistor $R_{CAL}$. The mux 112 connects the output of signal generator 116 to input of current measurement circuitry 126 through the resistor $R_{CAL}$. The measured current performed by current measurement circuitry is $I_{CAL}$. With the known resistance value of the resistor $R_{CAL}$, it is possible to derive the voltage $V_{CAL}=I_{CAL} \cdot R_{CAL}$ across the resistor $R_{CAL}$. The measured current $I_{CAL}$ and the known resistance value of resistor $R_{CAL}$ form equation 1, seen below. The voltage $V_{CAL}$ represents the (calibrated) peak voltage from signal generator 116. The measurement of the voltage $V_{CAL}$ across $R_{CAL}$ is determined by measuring a current through $R_{CAL}$, i.e., through the signal path that includes $R_{CAL}$, by current measurement circuitry 126.

FIGS. 5-9 illustrate five current measurements, according to embodiments of the disclosure. The five current measurements setup a system of five equations, and the five unknown impedances (the bio-impedance and the four contact impedances) can be derived from solving the system of five equations. Note that, in the individual branches, impedances in a cable connected to a pin and a contact impedance are lumped together and represented as a contact impedance (e.g., $Z_{E1}$, $Z_{E2}$, $Z_{E3}$, and $Z_{E4}$), for simplicity. The contact impedances thus represent individual branch impedances.

Figure 5:
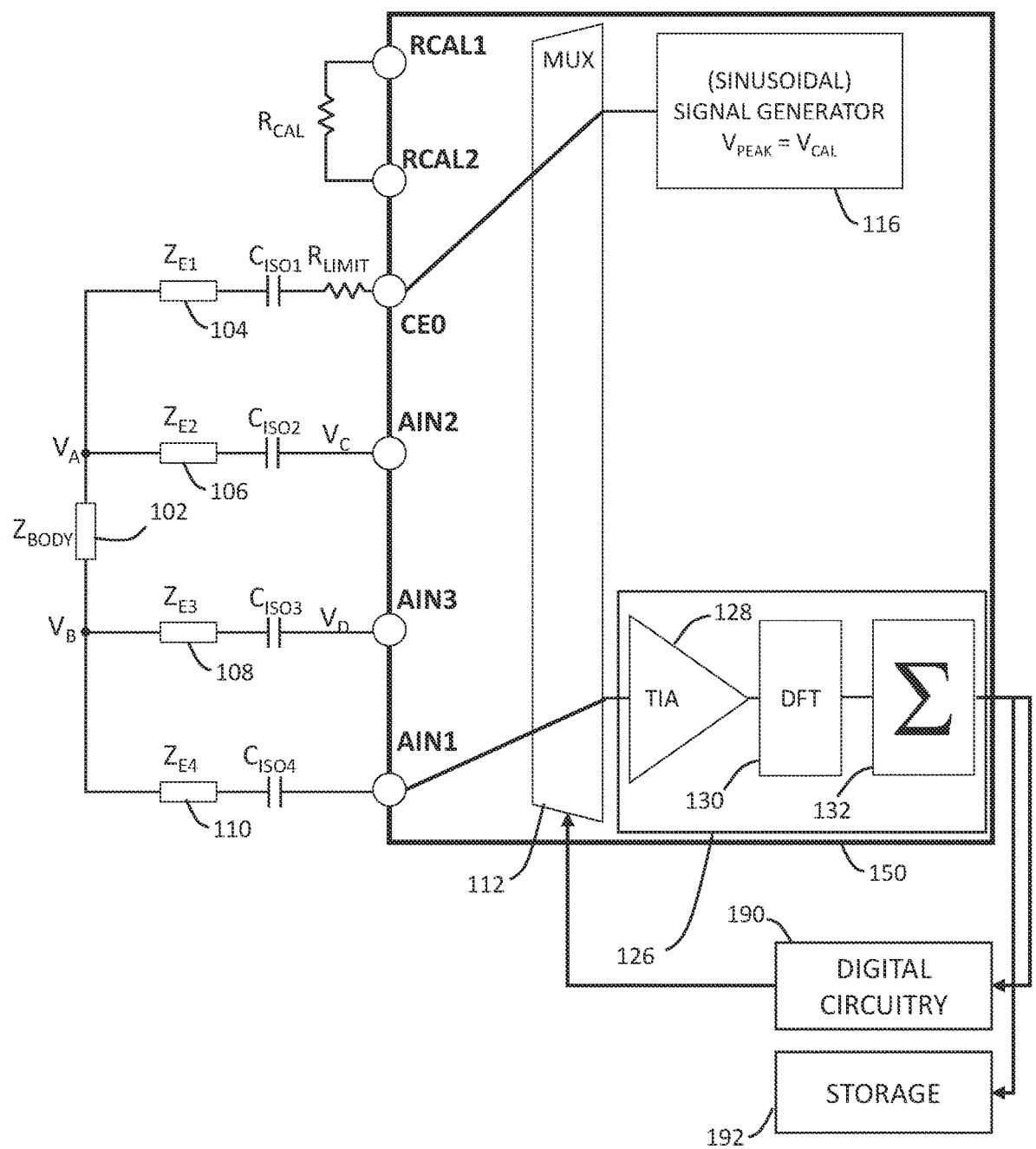
FIGS. 5-9 illustrate five current measurements, according to embodiments of the disclosure.

In FIG. 5, the mux 112 is configured to couple the signal path from pin CE0 to the output of the signal generator 116 and to couple the signal path from pin AIN1 to the input of the current measurement circuitry 126. The measured current obtained by current measurement circuitry 126 is $I_1$. The measured current $I_1$, measured current $I_{CAL}$, and the known resistance value of $R_{CAL}$ form equation 2, seen below. Mux 112 has formed a signal path from the signal generator 116 to the current measurement circuitry 126. The signal path includes unknown contact impedance $Z_{E1}$, unknown bio-impedance $Z_{BODY}$, and unknown contact impedance $Z_{E4}$ (in series). The signal path includes a branch with electrode 104 and pin CE0, and a branch with electrode 110 and pin AIN1. Equation 2 encapsulates the relationship between the three unknown impedances $Z_{E1}$, $Z_{BODY}$, and $Z_{E4}$ in the signal path and the measured current $I_1$, measured current $I_{CAL}$, and the known resistance value of $R_{CAL}$. Note that the product of the measured current $I_{CAL}$ and the known resistance value of $R_{CAL}$ is equivalent to the voltage $V_{CAL}$ obtained from the calibration measurement.

Figure 6:
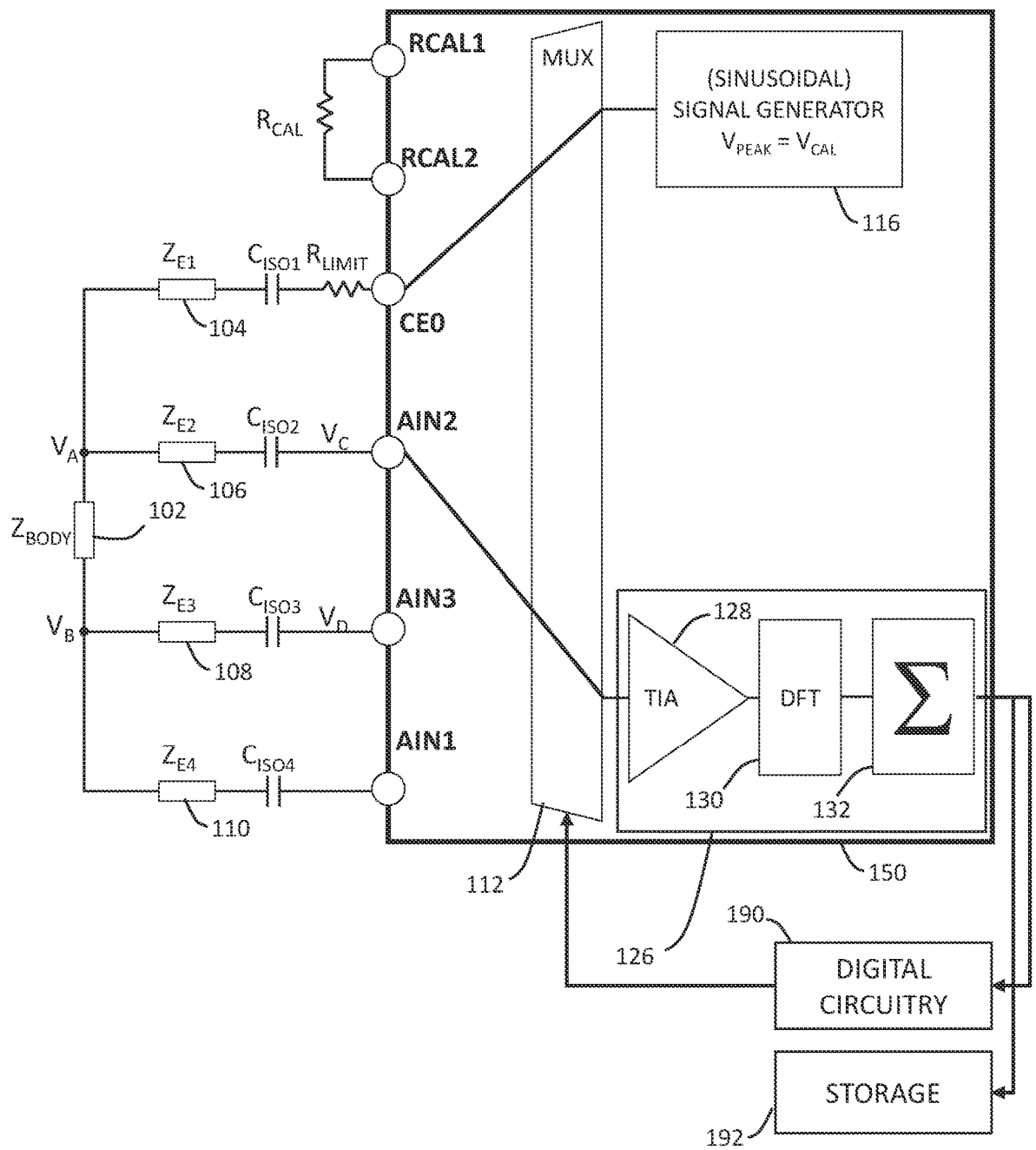

In FIG. 6, the mux 112 is configured to couple the signal path from pin CE0 to the output of the signal generator 116 and to couple the signal path from pin AIN2 to the input of the current measurement circuitry 126. The measured current obtained by current measurement circuitry 126 is $I_2$. The measured current $I_2$, measured current $I_{CAL}$, and the known resistance value of $R_{CAL}$ form equation 3, seen below. Mux 112 has formed a signal path from the signal generator 116 to the current measurement circuitry 126. The signal path includes unknown contact impedance $Z_{E1}$ and unknown contact impedance $Z_{E2}$ (in series). The signal path includes a branch with electrode 104 and pin CE0, and a branch with electrode 106 and pin AIN2. Equation 3 encapsulates the relationship between the two unknown impedances $Z_{E1}$ and $Z_{E2}$ in the signal path and the measured current $I_2$, measured current $I_{CAL}$, and the known resistance value of $R_{CAL}$.

Figure 7:
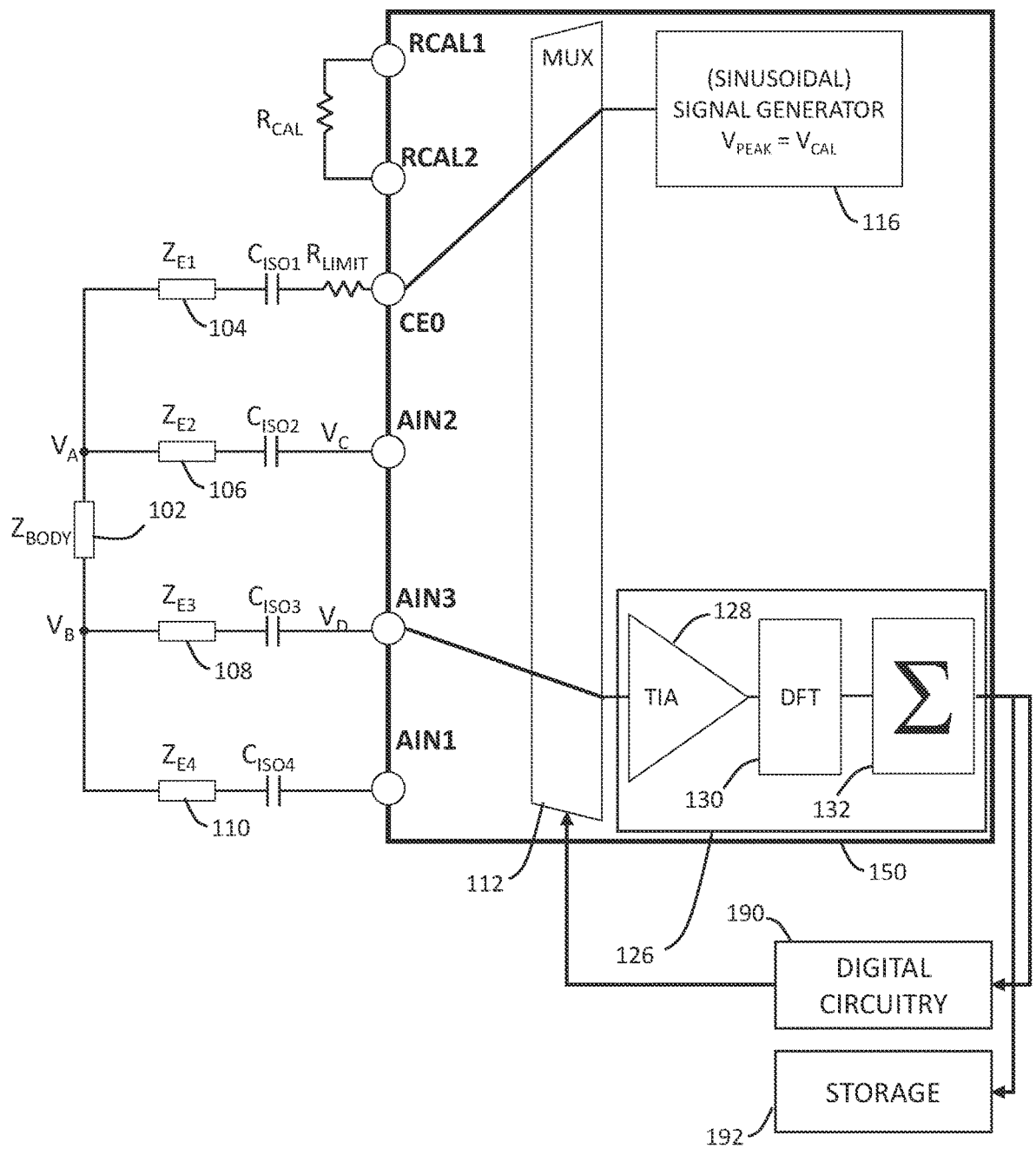

In FIG. 7, the mux 112 is configured to couple the signal path from pin CE0 to the output of the signal generator 116 and to couple the signal path from pin AIN3 to the input of the current measurement circuitry 126. The measured current obtained by current measurement circuitry 126 is $I_3$. The measured current $I_3$, measured current $I_{CAL}$, and the known resistance value of $R_{CAL}$ form equation 4, seen below. Mux 112 has formed a signal path from the signal generator 116 to the current measurement circuitry 126. The signal path includes unknown contact impedance $Z_{E1}$, unknown bio-impedance $Z_{BODY}$, and unknown contact impedance $Z_{E3}$ (in series). The signal path includes a branch with electrode 104 and pin CE0, and a branch with electrode 108 and pin AIN3. Equation 4 encapsulates the relationship between the three unknown impedances $Z_{E1}$, $Z_{BODY}$, and $Z_{E3}$ in the signal path and the measured current $I_3$, measured current Ica, and the known resistance value of $R_{CAL}$.

Figure 8:
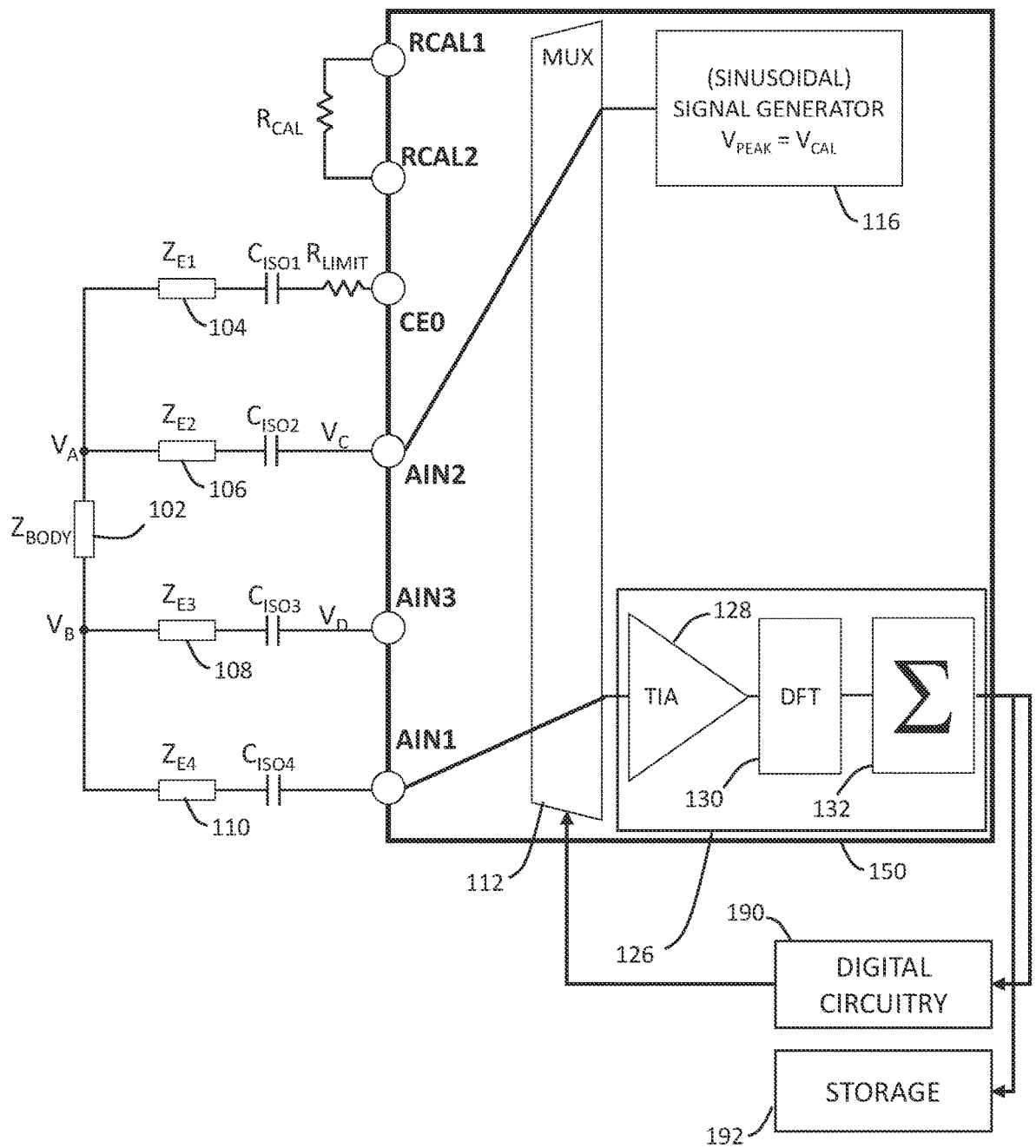

In FIG. 8, the mux 112 is configured to couple the signal path from pin AIN2 to the output of the signal generator 116 and to couple the signal path from pin AIN1 to the input of the current measurement circuitry 126. The measured current obtained by current measurement circuitry 126 is $I_4$. The measured current $I_4$, measured current Ica, and the known resistance value of $R_{CAL}$ form equation 5, seen below. Mux 112 has formed a signal path from the signal generator 116 to the current measurement circuitry 126. The signal path includes unknown contact impedance $Z_{E2}$, unknown bio-impedance $Z_{BODY}$, and unknown contact impedance $Z_{E4}$ (in series). The signal path includes a branch with electrode 106 and pin AIN2, and a branch with electrode 110 and pin AIN1. Equation 5 encapsulates the relationship between the three unknown impedances $Z_{E2}$, $Z_{BODY}$, and $Z_{E4}$ in the signal path and the measured current $I_4$, measured current Ica, and the known resistance value of $R_{CAL}$.

Figure 9:
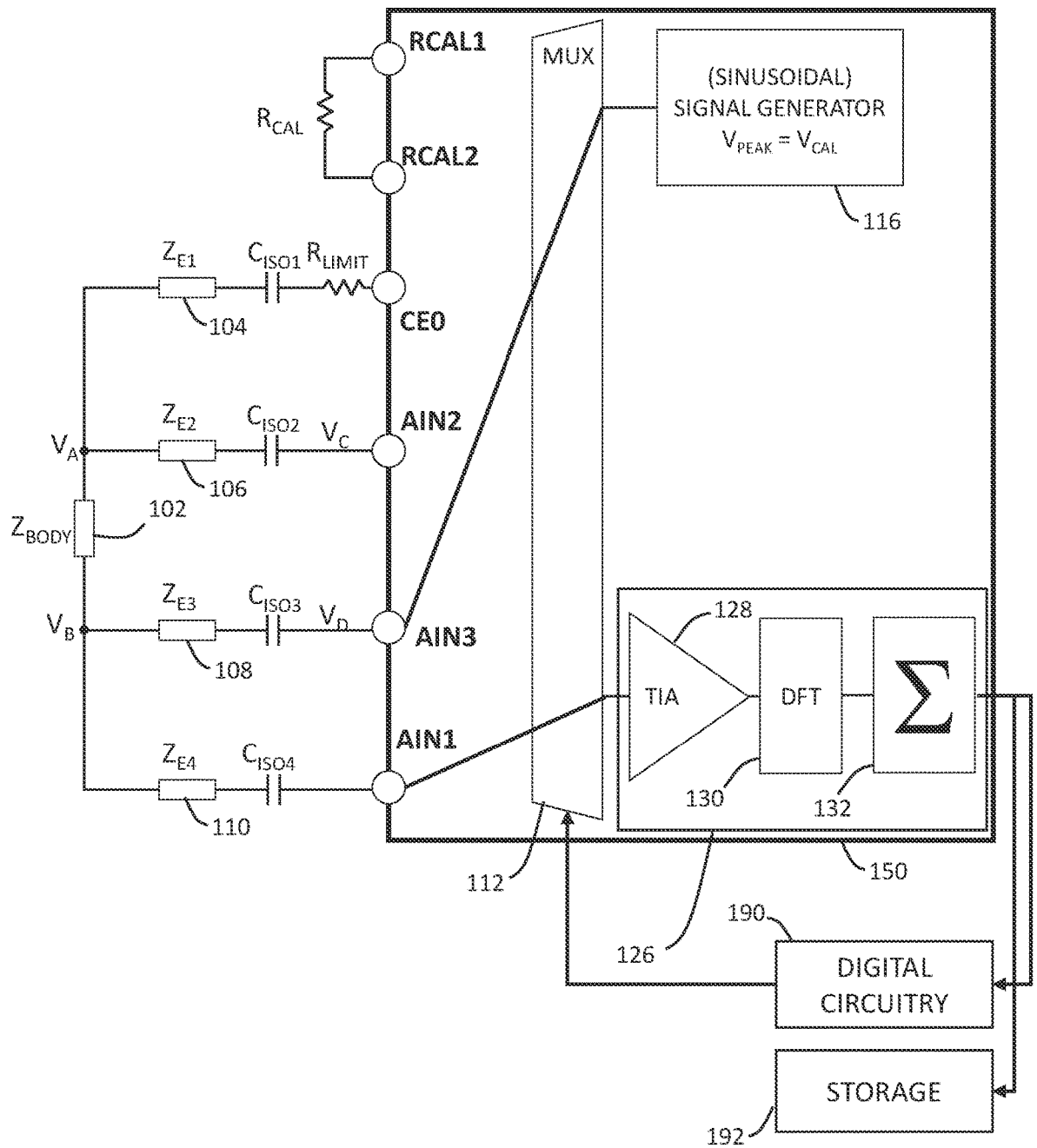

In FIG. 9, the mux 112 is configured to couple the signal path from pin AIN3 to the output of the signal generator 116 and to couple the signal path from pin AIN1 to the input of the current measurement circuitry 126. The measured current obtained by current measurement circuitry 126 is $I_5$. The measured current $I_5$, measured current $I_{CAL}$, and the known resistance value of $R_{CAL}$ form equation 6, seen below. Mux 112 has formed a signal path from the signal generator 116 to the current measurement circuitry 126. The signal path includes unknown contact impedance $Z_{E3}$ and unknown contact impedance $Z_{E4}$ (in series). The signal path includes a branch with electrode 108 and pin AIN3, and a branch with electrode 110 and pin AIN1. Equation 6 encapsulates the relationship between the two unknown impedances, $Z_{E3}$ and $Z_{E4}$, in the signal path and the measured current $I_5$, measured current $I_{CAL}$, and the known resistance value of $R_{CAL}$.

| | | |
|---|---|---|
| Calibration Measurement | $V_{CAL} = I_{CAL} \cdot R_{CAL}$ | (eq. 1) |
| Current Measurement (FIG. 5) | $Z_{E1} + 0 + Z_{BODY} + 0 + Z_{E4} = \dfrac{I_{CAL} \cdot R_{CAL}}{I_1}$ | (eq. 2) |
| Current Measurement (FIG. 6) | $Z_{E1} + Z_{E2} + 0 + 0 + 0 = \dfrac{I_{CAL} \cdot R_{CAL}}{I_2}$ | (eq. 3) |
| Current Measurement (FIG. 7) | $Z_{E1} + 0 + Z_{BODY} + Z_{E3} + 0 = \dfrac{I_{CAL} \cdot R_{CAL}}{I_3}$ | (eq. 4) |
| Current Measurement (FIG. 8) | $0 + Z_{E2} + Z_{BODY} + 0 + Z_{E4} = \dfrac{I_{CAL} \cdot R_{CAL}}{I_4}$ | (eq. 5) |
| Current Measurement (FIG. 9) | $0 + 0 + 0 + Z_{E3} + Z_{E4} = \dfrac{I_{CAL} \cdot R_{CAL}}{I_5}$ | (eq. 6) |

With five equations (equations 2-6) and five unknown impedances $Z_{BODY}$, $Z_{E1}$, $Z_{E2}$, $Z_{E3}$, and $Z_{E4}$, the values for the five unknown impedances $Z_{BODY}$, $Z_{E1}$, $Z_{E2}$, $Z_{E3}$, and $Z_{E4}$ can be derived and determined. As illustrated by FIGS. 5-9, each unique signal path includes two branch impedances. Moreover, as seen in FIGS. 5, 7, and 8, some of the unique signal paths can each include the bio-impedance and two branch impedances. Each unique signal path includes at least some of the unknown impedances, and together, the unique signal paths include each unknown impedance at least once.

The five equations (equations 2-6) can be rewritten to equations 7-11 that gives the unknown impedances $Z_{BODY}$, $Z_{E1}$, $Z_{E2}$, $Z_{E3}$, and $Z_{E4}$ in terms of one or more ones of the current measurements (one or more of $I_1$, $I_2$, $I_3$, $I_4$, and $I_5$), the measured current $I_{CAL}$, and the known resistance value of $R_{CAL}$. Digital circuitry 190, such as a microcontroller or microprocessor, can be implemented to compute the unknown impedances based on the measurements seen in FIGS. 4-9 and equations 7-11. Computer-readable storage 192 can store the measurements, and instructions for processing the measurements to derive the impedances.

$$Z_{E1} = \frac{I_{CAL} \cdot R_{CAL}}{2} \cdot \left( \frac{1}{I_1} + \frac{1}{I_2} - \frac{1}{I_4} \right) \qquad \text{(eq. 7)}$$

-continued $$Z_{E2} = \frac{I_{CAL} \cdot R_{CAL}}{2} \cdot \left(\frac{1}{I_2} + \frac{1}{I_4} - \frac{1}{I_1}\right) \quad \text{(eq. 8)}$$

$$Z_{E3} = \frac{I_{CAL} \cdot R_{CAL}}{2} \cdot \left(\frac{1}{I_3} + \frac{1}{I_5} - \frac{1}{I_1}\right) \quad \text{(eq. 9)}$$

$$Z_{E4} = \frac{I_{CAL} \cdot R_{CAL}}{2} \cdot \left(\frac{1}{I_1} + \frac{1}{I_5} - \frac{1}{I_3}\right) \quad \text{(eq. 10)}$$

$$Z_{BODY} = \frac{I_{CAL} \cdot R_{CAL}}{2} \cdot \left(\frac{1}{I_3} + \frac{1}{I_4} - \frac{1}{I_2} - \frac{1}{I_5}\right) \quad \text{(eq. 11)}$$

The measurements seen in FIGS. 4-9 can be performed in any order. In some cases, more than five measurements can be made to generate more than five equations.

The scheme illustrated by FIGS. 4-9 can have several advantages. Note that a voltage measurement across the unknown bio-impedance $Z_{BODY}$ is no longer needed (which is normally required in the four-wire impedance measurement illustrated by FIG. 1). As a result, an expensive inAmp 120 is no longer required in circuitry 150. Furthermore, the error due to the grounded capacitances at pins AIN2 and AIN3 (acting as a low pass filter), which causes the voltages of $V_A$ not being the same as $V_C$ and the voltages of $V_B$ not being the same as $V_D$, is no longer relevant since a voltage measurement is not being made. Moreover, the scheme can effectively derive five impedances $Z_{BODY}$, $Z_{E1}$, $Z_{E2}$, $Z_{E3}$, and $Z_{E4}$.

Figure 10:
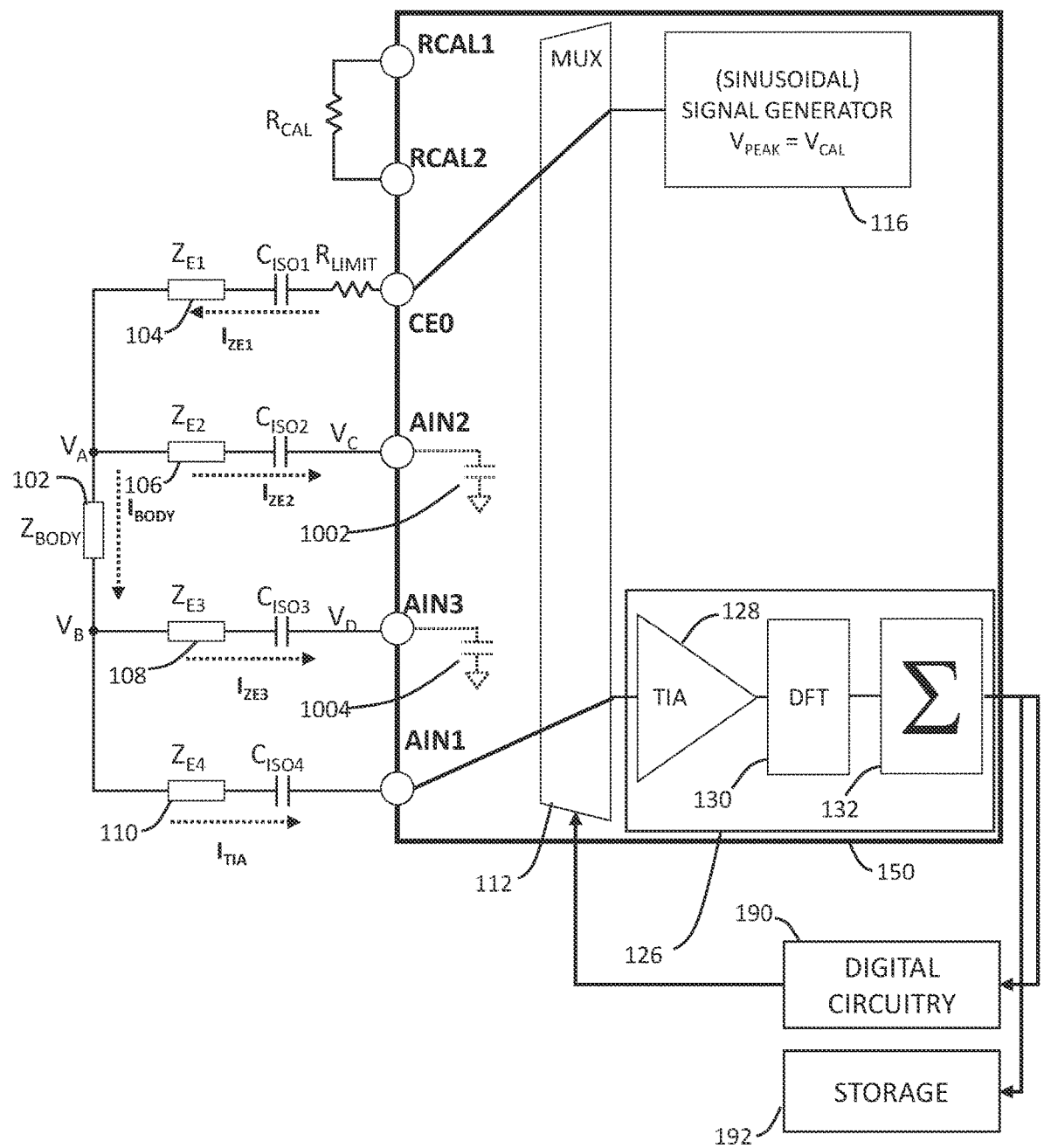
FIG. 10 illustrates current leakage present in the measurement seen in FIG. 5, according to some embodiments of the disclosure.

Another Exemplary Scheme for Deriving Contact Impedances Through Multiple Measurements and Signal Processing In the previous scheme illustrated by the measurements seen in FIGS. 4-9, there is one limitation: current leakage. FIG. 10 illustrates current leakage present in the measurement seen in FIG. 5, according to some embodiments of the disclosure. When making a current measurement, such as current $I_1$ (as illustrated by FIG. 5), the branches which are not connected to the signal generator 116 or the current measurement circuitry 126 ideally has infinite impedance. With infinite impedance, the branches which are not connected to the signal generator 116 or the current measurement circuitry 126 would have zero current. In other words, $I_{ZE2}$ (current through branch having electrode 106 and pin Ain2) and $I_{ZE3}$ (current through branch having electrode 108 and pin AIN3) are ideally zero. As a result, $I_{ZE1}$ would be equal to $I_{BODY}$ (current through the unknown bio-impedance), and would also be equal to $I_{TIA}$ (current through branch). This would mean that no current is leaking through the branches having electrode 106 and electrode 108, and the current measurement circuitry 126 is measuring the current through the unknown bio-impedance $Z_{BODY}$ accurately ($I_{TIA}=I_{BODY}$). In reality, the branches which are not connected to the signal generator 116 or the current measurement circuitry 126 do not have infinite impedances, and can have grounded capacitances 1002 and 1004 (e.g., in the pF or μF range). The grounded capacitances 1002 and 1004 represent circuitry (e.g., circuitry in mux 112) capable of sinking current in the branches. As a result, a part of the current $I_{ZE1}$ may flow through the branches which are not connected to the signal generator 116 or the current measurement circuitry 126. This means that $I_{ZE2}$ and $I_{ZE3}$ is not zero, and $I_{ZE1}$ may not be equal to $I_{BODY}$, and may not be equal to $I_{TIA}$. As a result, current is leaking through the branches having electrode 106 and electrode 108, and the current measurement circuitry 126 is measuring the current through the unknown bio-impedance $Z_{BODY}$ inaccurately ($I_{TIA} \neq I_{BODY}$).

To address this limitation, the current measurements setting up a system of equations having the unknown impedances can be modified. Specifically, the configuration of the mux 112 is adapted for each measurement, and a different system of equations is used for deriving the unknown impedances. Instead of leaving some of the signal paths floating, all signal paths are connected either to the signal generator 116 or the current measurement circuitry 126. The unique signal paths or unique impedance networks, instead of each including just a subset of the unknown impedances or just two of four branches, the unique signal paths or unique impedance networks would include all of the bio-impedance and the branch impedances, and all four branches. As a result, leaked current can be captured by the system of equations.

For four current measurements, one of the signal paths is connected to the signal generator 116, and the other three of the signal paths are connected to the current measurement circuitry 126. One of the four branches is connected to the output of signal generator 116, and three other ones of the four branches are connected to the input of current measurement circuitry 126. For another current measurement, two signal paths are connected to the signal generator 116, and the other two of the signal paths are connected to the current measurement circuitry 126. Two of the four branches are connected to the output of signal generator 116, and two other ones of the four branches are connected to the input of current measurement circuitry 126. Accordingly, no floating branches will cause current leakage or sink current. The five current measurements form a different system of equations, since the overall signal path formed by the mux 112 from the signal generator 116 to the current measurement circuitry 126 now involves parallel impedances (i.e., parallel unknown impedances). However, the system of equations having five equations can still enable the five unknown impedances to be determined.

By configuring mux 112 and making multiple current measurements, it is possible to derive the unknown impedances of the system, including the unknown bio-impedance $Z_{BODY}$, and the contact impedances $Z_{E1}$, $Z_{E2}$, $Z_{E3}$, and $Z_{E4}$, based on a system of equations. The system of equations are formed through a calibration measurement, and several current measurements of different, unique signal paths formed by configuring mux 112. Mux 112 can selectively couple the output of the signal generator 116 and the input of the current measurement circuitry 126 to different pins (e.g., RCAL1, RCAL2, CE0, AIN2, AIN3, and AIN1). Accordingly, mux 112 can connect the output of the signal generator 116 to the input of the current measurement circuitry 126 through different signal paths, or different impedance networks involving all of the unknown impedances. The different, unique signal paths, form unique impedance networks, where each unique impedance network combines all of the unknown impedances of the system: the unknown bio-impedance $Z_{BODY}$, and the contact impedances $Z_{E1}$, $Z_{E2}$, $Z_{E3}$, and $Z_{E4}$, with a unique topology. Unique signal paths or unique impedance networks each involving all of the unknown impedances, and the current measurements of the unique signal paths or unique impedance networks, setup a system of equations for the unknown impedances. Effectively, the signal generator 116 can excite unique signal paths or unique impedance networks formed by mux 112, and the current measurement circuitry 126 can make measurements of current going through the unique signal paths or unique impedance networks.

To determine five unknown impedances (the bio-impedance and the four contact impedances), at least five equations are needed. With a sufficient number of equations, it is possible to derive the five unknown impedances through signal processing (i.e., calculations). Through suitable processing, the current measurements allow the bio-impedance and the contact impedances to be determined. The current measurements can be performed by the current measurement circuitry 126. The signal processing can be performed in the digital domain, e.g., by digital circuitry 190. Digital circuitry 190 can include specialized digital hardware to perform the signal processing. Digital circuitry 190 can include a microprocessor or microcontroller configured to carry out instructions that implement the signal processing. The digital circuitry 190 can be provided on-chip with circuitry 150 or off-chip (as shown). Digital circuitry 190 can be implemented to control mux 112 to form unique signal paths or unique impedance networks from the signal generator 116 to the current measurement circuitry 126. Computer-readable storage 192 can store the measurements. Computer-readable storage 192 can store the instructions that implement the signal processing. The computer-readable storage 192 can be provided on-chip with circuitry 150 or off-chip (as shown).

In this modified scheme, the calibration measurement can be performed based on the configuration seen in FIG. 4 and equation 1, which yields $V_{CAL}$. FIGS. 11-15 illustrate five current measurements, according to embodiments of the disclosure. The five current measurements setup a system of five equations, and the five unknown impedances (the bio-impedance and the four contact impedances) can be derived from solving the system of five equations. Note that, in the individual branches, impedances in a cable connected to a pin is lumped together and represented as a contact impedance (e.g., $Z_{E1}$, $Z_{E2}$, $Z_{E3}$, and $Z_{E4}$), for simplicity. The contact impedances thus represent individual branch impedances.

Figure 11:
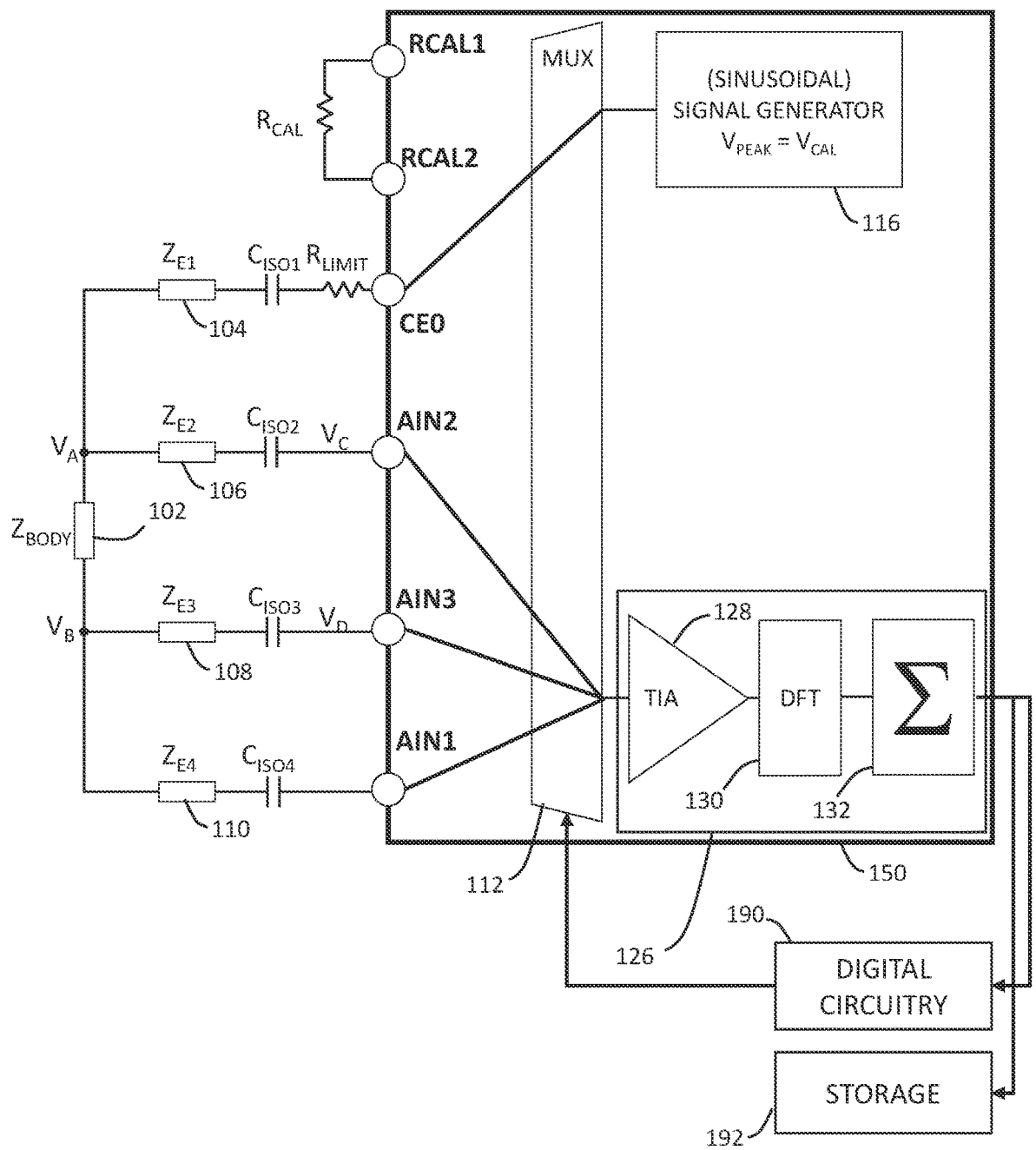
FIGS. 11-15 illustrate five current measurements which avoid current leakage, according to embodiments of the disclosure.

In FIG. 11, the mux 112 is configured to couple the signal path from pin CE0 to the output of the signal generator 116, to couple the signal path from pin AIN2 to the input of current measurement circuitry 126, to couple the signal path from pin AIN3 to the input of current measurement circuitry 126, to couple the signal path from pin AIN1 to the input of current measurement circuitry 126. The measured current done by current measurement circuitry 126 is $I_1$. The configuration of mux 112 in FIG. 11 forms an overall signal path that includes $Z_{E1}$ in series with ($Z_{E2}$ in parallel with ($Z_{BODY}$ in series with ($Z_{E3}$ and $Z_{E4}$ in parallel)). The branch with electrode 104 and pin CE0 is connected to the output of the signal generator 116. The branch with electrode 106 and pin AIN2 is connected to the input of current measurement circuitry 126. The branch with electrode 108 and pin AIN3 is connected to the input of current measurement circuitry 126. The branch with electrode 110 and pin AIN1 is connected to the input of current measurement circuitry 126. The measured current $I_1$, measured voltage $V_{CAL}$, form equation 12, seen below. Equation 12 encapsulates the relationship between the measured current $I_1$, measured voltage $V_{CAL}$, and the unknown impedances in the overall signal path from the signal generator 116 to current measurement circuitry 126 (formed by the mux 112 in the configuration shown in FIG. 11).

Figure 12:
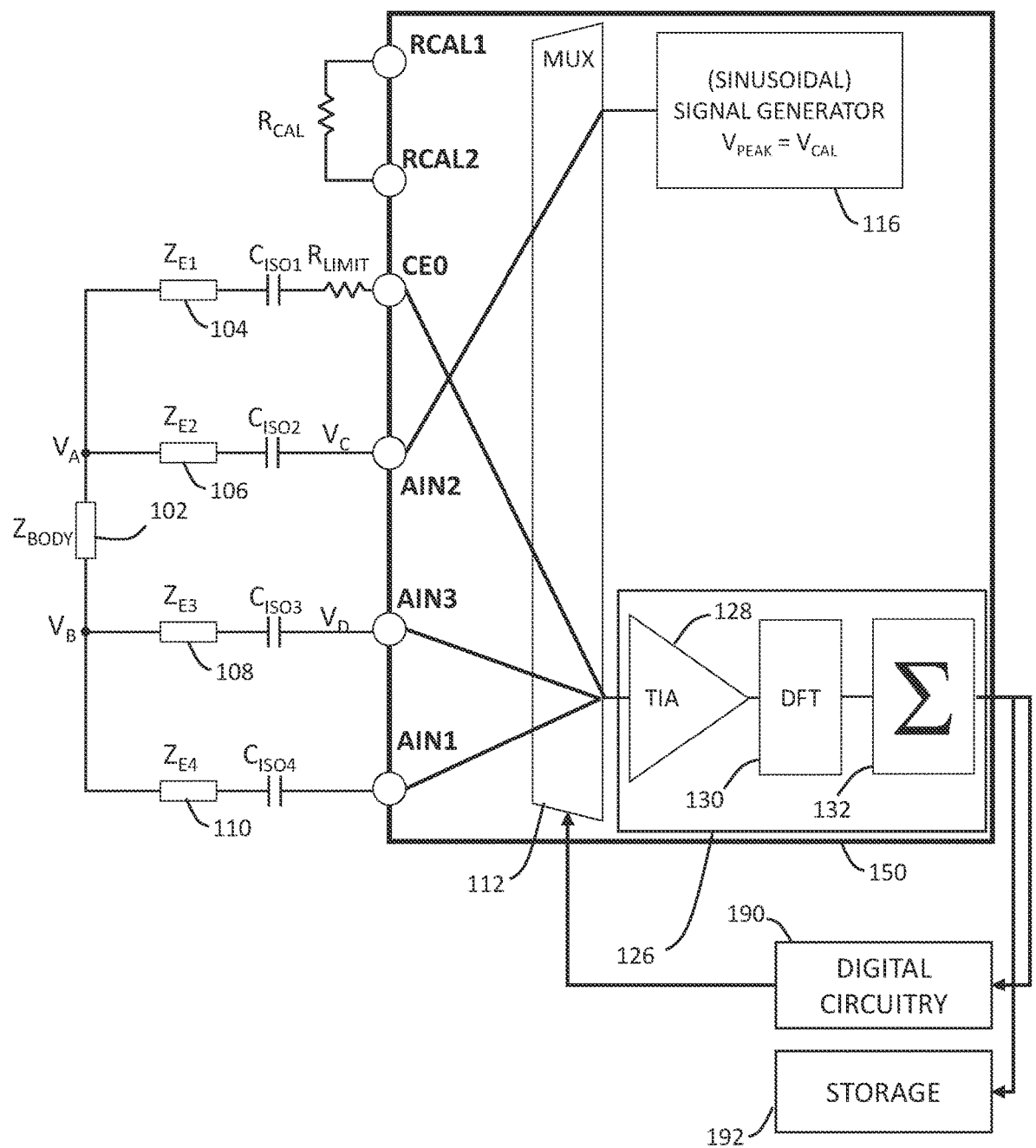

In FIG. 12, the mux 112 is configured to couple the signal path from pin AIN2 to the output of signal generator 116, to couple the signal path from pin CE0 to the input of current measurement circuitry 126, to couple the signal path from pin AIN3 to the input of current measurement circuitry 126, to couple the signal path from pin AIN1 to the input of current measurement circuitry 126. The measured current done by current measurement circuitry 126 is $I_2$. The configuration of mux 112 in FIG. 12 forms an overall signal path that includes $Z_{E2}$ in series with ($Z_{E1}$ in parallel with ($Z_{BODY}$ in series with ($Z_{E3}$ and $Z_{E4}$ in parallel))). The branch with electrode 104 and pin CE0 is connected to the input of the current measurement circuitry 126. The branch with electrode 106 and pin AIN2 is connected to the output of signal generator 116. The branch with electrode 108 and pin AIN3 is connected to the input of current measurement circuitry 126. The branch with electrode 110 and pin AIN1 is connected to the input of current measurement circuitry 126. The measured current $I_2$, measured voltage $V_{CAL}$, form equation 13, seen below. Equation 13 encapsulates the relationship between the measured current $I_2$, measured voltage $V_{CAL}$, and the unknown impedances in the overall signal path from the signal generator 116 to current measurement circuitry 126 (formed by the mux 112 in the configuration shown in FIG. 12).

Figure 13:
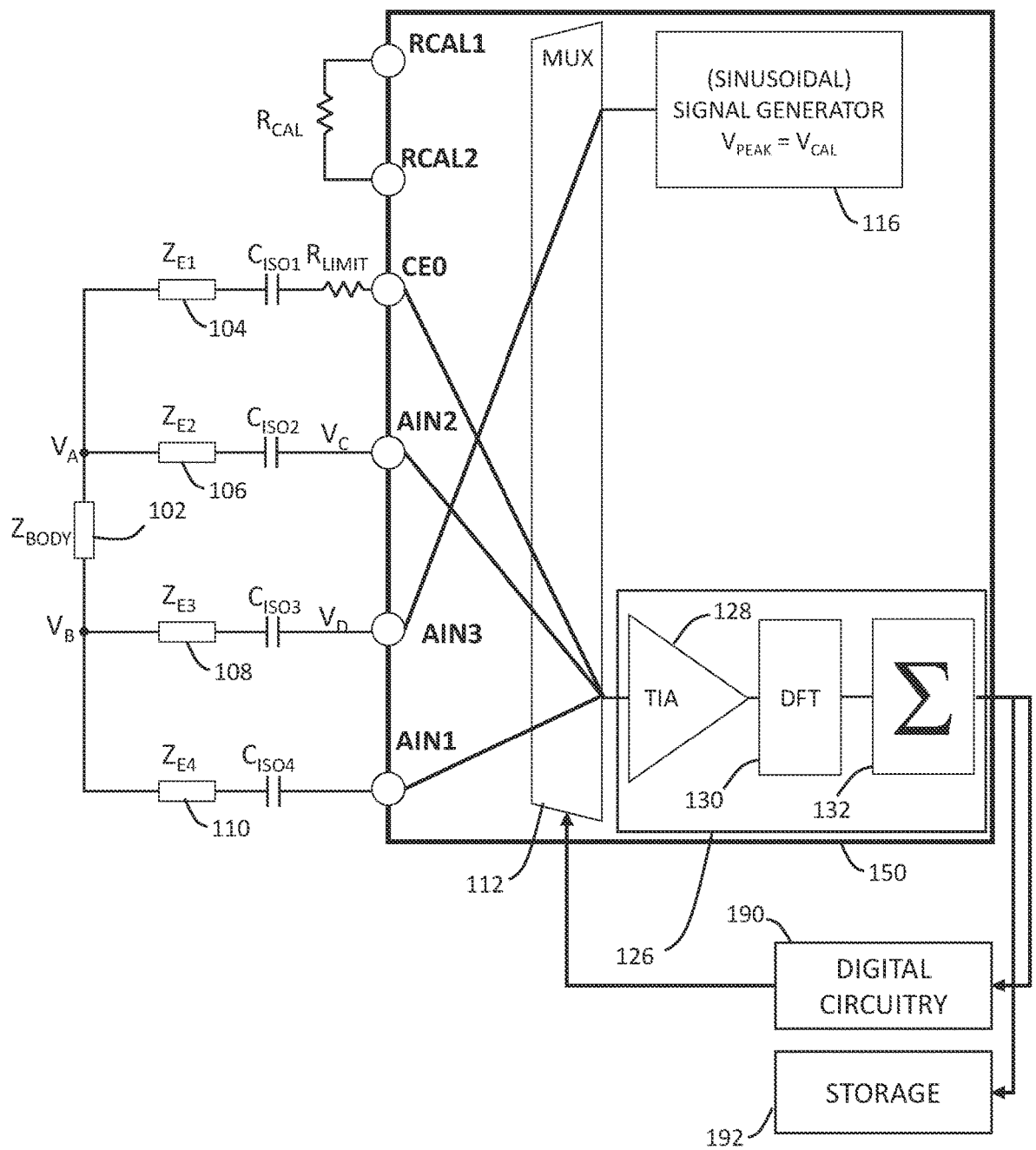

In FIG. 13, the mux 112 is configured to couple the signal path from pin AIN3 to the output of signal generator 116, to couple the signal path from pin CE0 to the input of current measurement circuitry 126, to couple the signal path from pin AIN2 to the input of current measurement circuitry 126, to couple the signal path from pin AIN1 to the input of current measurement circuitry 126. The measured current done by current measurement circuitry 126 is $I_3$. The configuration of mux 112 in FIG. 13 forms an overall signal path that includes $Z_{E3}$ in series with ($Z_{E4}$ in parallel with ($Z_{BODY}$ in series with ($Z_{E1}$ and $Z_{E2}$ in parallel))). The branch with electrode 104 and pin CE0 is connected to the input of the current measurement circuitry 126. The branch with electrode 106 and pin AIN2 is connected to input of the current measurement circuitry 126. The branch with electrode 108 and pin AIN3 is connected to the output of signal generator 116. The branch with electrode 110 and pin AIN1 is connected to the input of current measurement circuitry 126. The measured current $I_3$, measured voltage $V_{CAL}$, form equation 14, seen below. Equation 14 encapsulates the relationship between the measured current $I_3$, measured voltage $V_{CAL}$, and the unknown impedances in the overall signal path from the signal generator 116 to current measurement circuitry 126 (formed by the mux 112 in the configuration shown in FIG. 13).

Figure 14:
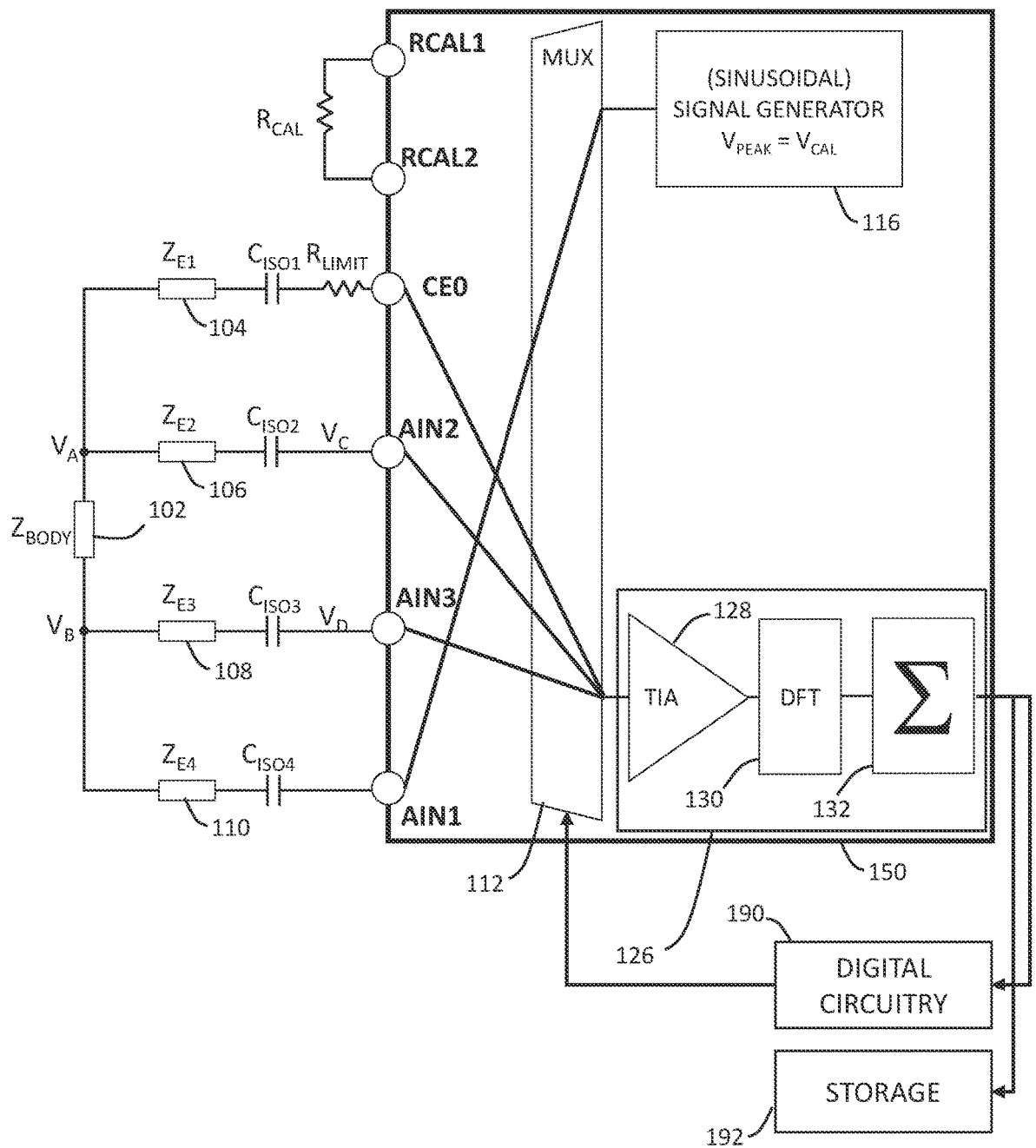

In FIG. 14, the mux 112 is configured to couple the signal path from pin AIN1 to the signal generator 116, to couple the signal path from pin CE0 to the current measurement circuitry 126, to couple the signal path from pin AIN2 to the current measurement circuitry 126, to couple the signal path from pin AIN3 to the current measurement circuitry 126. The measured current done by current measurement circuitry 126 is $I_4$. The configuration of mux 112 in FIG. 14 forms an overall signal path that includes $Z_{E4}$ in series with ($Z_{E3}$ in parallel with ($Z_{BODY}$ in series with ($Z_{E1}$ and $Z_{E2}$ in parallel))). The branch with electrode 104 and pin CE0 is connected to the input of the current measurement circuitry 126. The branch with electrode 106 and pin AIN2 is connected to input of the current measurement circuitry 126. The branch with electrode 108 and pin AIN3 is connected to the input of current measurement circuitry 126. The branch with electrode 110 and pin AIN1 is connected to the output of signal generator 116. The measured current $I_4$, measured voltage $V_{CAL}$, form equation 15, seen below. Equation 15 encapsulates the relationship between the measured current $I_4$, measured voltage $V_{CAL}$, and the unknown impedances in the overall signal path from the signal generator 116 to current measurement circuitry 126 (formed by the mux 112 in the configuration shown in FIG. 14).

Figure 15:
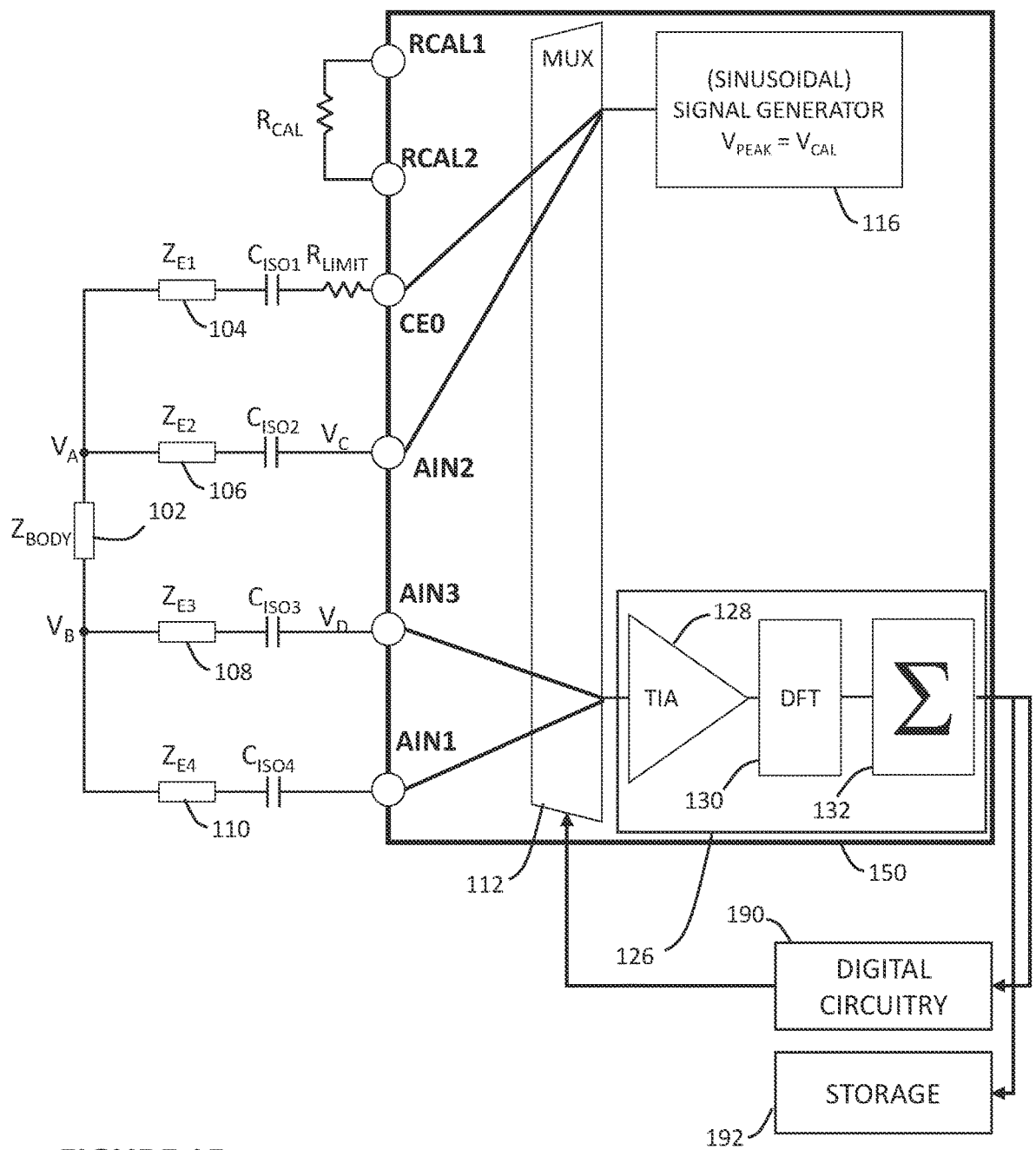

In FIG. 15, the mux 112 is configured to couple the signal path from pin CE0 to the signal generator 116, to couple the signal path from pin AIN2 to the signal generator 116 (as well), to couple the signal path from pin AIN3 to the current measurement circuitry 126, to couple the signal path from pin AIN1 to the current measurement circuitry 126. The measured current done by current measurement circuitry 126 is $I_5$. The configuration of mux 112 in FIG. 15 forms an overall signal path that includes ($Z_{E1}$ and $Z_{E2}$ in parallel) in series with $Z_{BODY}$ and in series with ($Z_{E3}$ and $Z_{E4}$ in parallel). The branch with electrode 104 and pin CE0 is connected to the output of the output of signal generator 116. The branch with electrode 106 and pin AIN2 is connected to the output of the output of signal generator 116. The branch with electrode 108 and pin AIN3 is connected to the input of current measurement circuitry 126. The branch with electrode 110 and pin AIN1 is connected to the input of current measurement circuitry 126. The measured current Is, measured voltage $V_{CAL}$, form equation 16, seen below. Equation 16 encapsulates the relationship between the measured current Is, measured voltage $V_{CAL}$, and the unknown impedances in the overall signal path from the signal generator 116 to current measurement circuitry 126 (formed by the mux 112 in the configuration shown in FIG. 15).

An alternative to the signal path illustrated by FIG. 15 is to connect the branch with electrode 104 and pin CE0 and the branch with electrode 106 and pin AIN2 is connected to the input of current measurement circuitry 126, and to connect the branch with electrode 108 and pin AIN3 and the branch with electrode 110 and pin AIN1 to the output of signal generator 116.

Current Measurement (FIG. 11)
$$I_1 = \frac{V_{CAL}}{Z_{E1} + (Z_{E2} \,//\, (Z_{BODY} + (Z_{E3} \,//\, Z_{E4})))} \quad \text{(eq. 12)}$$

Current Measurement (FIG. 12)
$$I_2 = \frac{V_{CAL}}{Z_{E2} + (Z_{E1} \,//\, (Z_{BODY} + (Z_{E3} \,//\, Z_{E4})))} \quad \text{(eq. 13)}$$

Current Measurement (FIG. 13)
$$I_3 = \frac{V_{CAL}}{Z_{E3} + (Z_{E4} \,//\, (Z_{BODY} + (Z_{E1} \,//\, Z_{E2})))} \quad \text{(eq. 14)}$$

Current Measurement (FIG. 14)
$$I_4 = \frac{V_{CAL}}{Z_{E4} + (Z_{E3} \,//\, (Z_{BODY} + (Z_{E1} \,//\, Z_{E2})))} \quad \text{(eq. 15)}$$

Current Measurement (FIG. 15)
$$I_5 = \frac{V_{CAL}}{(Z_{E1} \,//\, Z_{E2}) + Z_{BODY} + (Z_{E3} \,//\, Z_{E4})} \quad \text{(eq. 16)}$$

Notation for parallel impedances: $Z_1 \,//\, Z_2 \equiv \dfrac{Z_1 Z_2}{Z_1 + Z_2}$ Current Measurement (FIG. 11)
$$I_1 = \frac{V_{CAL}}{Z_{E1} + \dfrac{Z_{E2} \cdot (Z_{E3} Z_{E4} + Z_{BODY} Z_{E3} + Z_{BODY} Z_{E4})}{Z_{E2} Z_{E3} + Z_{E2} Z_{E4} + Z_{E3} Z_{E4} + Z_{BODY} Z_{E3} + Z_{BODY} Z_{E4}}} \quad \text{(eq. 17)}$$

Current Measurement (FIG. 12)
$$I_2 = \frac{V_{CAL}}{Z_{E2} + \dfrac{Z_{E1} \cdot (Z_{E3} Z_{E4} + Z_{BODY} Z_{E3} + Z_{BODY} Z_{E4})}{Z_{E1} Z_{E3} + Z_{E1} Z_{E4} + Z_{E3} Z_{E4} + Z_{BODY} Z_{E3} + Z_{BODY} Z_{E4}}} \quad \text{(eq. 18)}$$

Current Measurement (FIG. 13)
$$I_3 = \frac{V_{CAL}}{Z_{E3} + \dfrac{Z_{E4} \cdot (Z_{E1} Z_{E2} + Z_{BODY} Z_{E1} + Z_{BODY} Z_{E2})}{Z_{E4} Z_{E1} + Z_{E4} Z_{E2} + Z_{E1} Z_{E2} + Z_{BODY} Z_{E1} + Z_{BODY} Z_{E2}}} \quad \text{(eq. 19)}$$

Current Measurement (FIG. 14)
$$I_4 = \frac{V_{CAL}}{Z_{E4} + \dfrac{Z_{E3} \cdot (Z_{E1} Z_{E2} + Z_{BODY} Z_{E1} + Z_{BODY} Z_{E2})}{Z_{E3} Z_{E1} + Z_{E3} Z_{E2} + Z_{E1} Z_{E2} + Z_{BODY} Z_{E1} + Z_{BODY} Z_{E2}}} \quad \text{(eq. 20)}$$

Current Measurement (FIG. 15)
$$I_5 = \frac{V_{CAL}}{Z_{BODY} + \dfrac{Z_{E1} Z_{E2}}{Z_{E1} + Z_{E2}} + \dfrac{Z_{E3} Z_{E4}}{Z_{E3} + Z_{E4}}} \quad \text{(eq. 21)}$$

Equations 17-21 show equations 12-16 in an expanded form based on the notation for parallel impedances.

With five equations (equations 12-16) and five unknown impedances $Z_{BODY}$, $Z_{E1}$, $Z_{E2}$, $Z_{E3}$, and $Z_{E4}$, the values for the five unknown impedances $Z_{BODY}$, $Z_{E1}$, $Z_{E2}$, $Z_{E3}$, and $Z_{E4}$ can be derived and determined. As illustrated by FIGS. 11-15, each unique signal path includes all of the unknown impedances. Moreover, as seen in FIGS. 5, 7, and 8, some of the unique signal paths can each include the bio-impedance and two branch impedances. Each unique signal path includes at least some of the unknown impedances, and together, the unique signal paths include each unknown impedance at least once.

Algebraic manipulations can be applied to equations 17-21 to rewrite equations 12-21 so that the unknown impedances $Z_{BODY}$, $Z_{E1}$, $Z_{E2}$, $Z_{E3}$, and $Z_{E4}$ are defined in terms of the current measurements (e.g., $I_1$, $I_2$, $I_3$, $I_4$, and $I_5$), the measured current $I_{CAL}$, and the known resistance value of $R_{CAL}$. The following pseudocode can be implemented in digital circuitry 190, such as a microcontroller or microprocessor, to determine and compute the unknown impedances based on the measurements seen in FIGS. 4, and 11-15.

```
vcal = RCAL* ICAL; // calibration measurement illustrated
by FIG. 4
a1 = vcal / I1; // current measurement illustrated by FIG. 11
a2 = vcal / I2; // current measurement illustrated by FIG. 12
a3 = vcal / I3; // current measurement illustrated by FIG. 13
a4 = vcal / I4; // current measurement illustrated by FIG. 14
a5 = vcal / I5; // current measurement illustrated by FIG. 15
E1 = -2*a1*a2*a5*(a1*a2 + a1*a5 - a2*a5)/(a1*a1*a2*a2 -
2*a1*a1*a2*a5 + a1*a1*a5*a5 - 2*a1*a2*a2*a5 -
2*a1*a2*a5*a5 + a2*a2*a5*a5); // derives Z_E1
E2 = -2*a1*a2*a5*(a1*a2 - a1*a5 + a2*a5)/(a1*a1*a2*a2 -
2*a1*a1*a2*a5 + a1*a1*a5*a5 - 2*a1*a2*a2*a5 -
2*a1*a2*a5*a5 + a2*a2*a5*a5); // derives Z_E2
E3 = -2*a3*a4*a5*(a3*a4 + a3*a5 - a4*a5)/(a3*a3*a4*a4 -
2*a3*a3*a4*a5 + a3*a3*a5*a5 - 2*a3*a4*a4*a5 -
2*a3*a4*a5*a5 + a4*a4*a5*a5); // derives Z_E3
E4 = -2*a3*a4*a5*(a3*a4 - a3*a5 + a4*a5)/(a3*a3*a4*a4 -
2*a3*a3*a4*a5 + a3*a3*a5*a5 - 2*a3*a4*a4*a5 -
2*a3*a4*a5*a5 + a4*a4*a5*a5); // derives Z_E4
ZB = (-E1*E2*E3 - E1*E2*E4 - E1*E3*E4 + E1*E3*a5 +
E1*E4*a5 - E2*E3*E4 + E2*E3*a5 +
E2*E4*a5)/(E1*E3 + E1*E4 + E2*E3 +
E2*E4); // derives Z_BODY
```

The measurements seen in FIGS. 4, and 11-15 can be performed in any order. In some cases, more than five measurements can be made to generate more than five equations.

The scheme illustrated by FIGS. 4, and 11-15 can have several advantages (similar to the scheme seen in FIGS. 4-9). Note that a voltage measurement across the unknown bio-impedance $Z_{BODY}$ is no longer needed (which is normally required in the four-wire impedance measurement illustrated by FIG. 1). As a result, an expensive inAmp 120 is no longer required in circuitry 150. Furthermore, the error due to the grounded capacitances at pins AIN2 and AIN3 (acting as a low pass filter), which causes to the voltages of $V_A$ not being the same as $V_C$ and the voltages of $V_B$ not being the same as $V_D$, is no longer relevant since a voltage measurement is not being made. Moreover, the scheme can effectively and accurately derive five impedances $Z_{BODY}$, $Z_{E1}$, $Z_{E2}$, $Z_{E3}$, and $Z_{E4}$. In addition to these advantages, this scheme can now ensure accuracy even in the presence of high impedances, and big imbalances between contact impedances.

Additional Technical Advantages

Measuring bio-impedance can be particularly useful for measuring body impedance for detecting fluid level of the lungs or measuring thoracic impedance. Measuring bio-impedance can also be useful in electrical impedance tomography to determine a composition of the body (e.g., imaging of tissues and bones) in a non-invasive manner by making bio-impedance measurements at different frequencies. Measuring bio-impedance can be useful in measuring respiration activity, where respiration activity can be obtained by observing variation in thorax impedance. Measuring bio-impedance and the contact impedances means that respiration activity can be obtained even in the presence of motion, since variations in contact impedances can be taken into account. Users such as athletes and patients can greatly benefit from such applications.

Knowing the contact impedances $Z_{E1}$, $Z_{E2}$, $Z_{E3}$, and $Z_{E4}$ in addition to the unknown bio-impedance $Z_{BODY}$ can enable the circuitry to infer whether the contacts (i.e., contacts being formed by the electrodes contacting the body) are good or not, e.g., as part of a diagnostic process. For instance, high contact impedances can indicate that patches/electrodes are not properly attached to the body. Accordingly, information about the quality of the contacts can be inferred from derived contact impedances.

For example, the digital circuitry 190 can determine quality of contacts corresponding to the four electrodes based on the impedances of the four branches. If a given impedance of a branch is too high, the digital circuitry 190 can infer that the contact for the branch is bad and output a signal that indicates the presence of a bad contact and optionally an identifier that identifies which contact is bad. The digital circuitry 190 can compare the impedances of the four branches against predetermined threshold(s) to determine whether a given impedance is too high.

User feedback can be provided based on the inferred information about the quality of the contacts. In another instance, smart drug delivery applications may require proper contacts to the body to ensure correct and effective drug delivery. If the contact is improper, drug can pool on the skin due to poor absorption and contact to the skin. Other applications, such as electrocardiography or defibrillation, may also require proper contacts to the body. Being able to infer the quality of the contacts based on the derived contact impedances can provide feedback to the user regarding the quality of the contacts in such contexts as well.

Some efforts to extract contact quality or contact impedance have limitations, and the schemes for measuring impedances described herein can improve upon those efforts. In some systems, efforts to extract contact quality or contact impedance ignore bio-impedance, or assume that the bio-impedance is zero, close to zero, or very small compared to the contact impedances. This assumption can be reasonable when the electrodes are measuring electrical activity of the heart, since in such situations, the electrodes are placed close to each other (e.g., on the thorax) and the skin has been prepared to make the body impedance very small. The impedances measurement schemes described herein do not make such an assumption. Not making this assumption can be beneficial in contexts where the body impedance can be large. For instance, body impedance cannot be ignored when electrodes are placed on other parts of the body, far apart from each other, where the bio-impedance can be in the range of the contact impedances. In another instance, the bio-impedance can be much greater than the contact impedances if the electrodes have very low impedances. In yet another instance, the lack of skin preparation can also make the contact impedances much larger than the bio-impedance being measured. For all these reasons, the impedances measurement schemes described herein can be used in a variety of situations. For instance, the impedances measurement scheme can be used to, non-invasively, obtain the body's composition, determine thoracic impedance, determine respiration activity in the presence of motion, etc.

Method for Measuring Impedances

Figure 16:
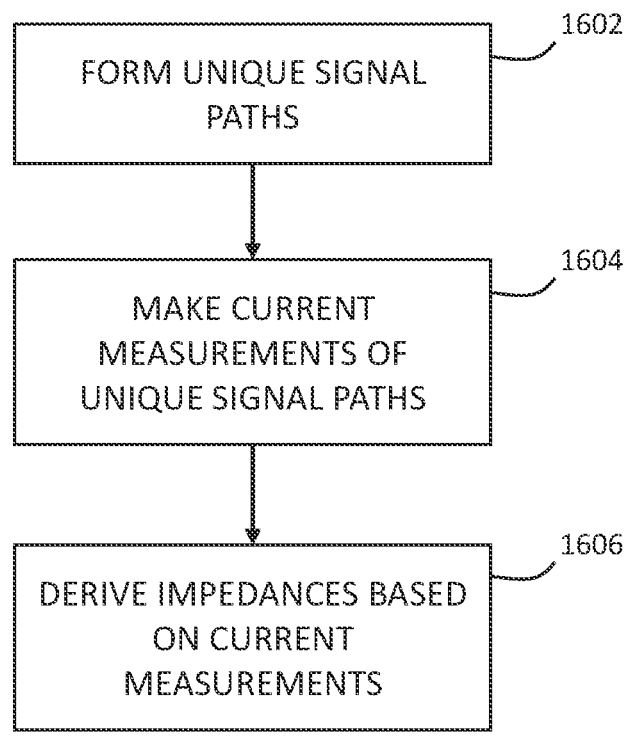
FIG. 16 is a flow diagram illustrating a method for measuring impedances, according to some embodiments of the disclosure.

FIG. 16 is a flow diagram illustrating a method for measuring impedances, according to some embodiments of the disclosure. The impedances include a bio-impedance and four branch impedances. In 1602, circuitry such as mux 112 can form unique signal paths. In 1604, current measurement circuitry 126 can make current measurements of the unique signal paths. The unique signal paths setup a system of equations that enables the impedances to be derived. To ensure the system of equations would yield the unknown impedances, each unique signal path includes at least some of the impedances, the unique signal paths include each impedance at least once. In 1606, digital circuitry 190 can derive the impedances based on the current measurements.

EXAMPLES

Example 1 is a method for measuring impedances, comprising: forming unique signal paths, wherein each unique signal path includes at least some of the impedances, the unique signal paths include each impedance at least once, and the impedances include a bio-impedance and four branch impedances, making current measurements of the unique signal paths, and deriving the impedances based on the current measurements.

In Example 2, the method of Example 1 can optionally include: deriving a voltage from a signal generator by applying an output of the signal generator to a resistor having known resistance value and measuring a current through the resistor, and deriving the impedances based further on the voltage from the signal generator.

In Example 3, the method of Example 1 or 2 can optionally include forming signal paths comprising: controlling a configurable network to connect an output of a signal generator to the unique signal paths and to connect an input of a current measurement circuitry to the unique signal paths.

In Example 4, the method of any one of Examples 1-3 can optionally include making the current measurements comprising: applying a signal from a signal generator to the unique signal paths, and measuring a current through each unique signal paths by a current measurement circuitry.

In Example 5, the method of any one of Examples 1-4 can optionally include each unique signal path including two branch impedances.

In Example 6, the method of any one of Examples 1-5 can optionally include each one of some of the unique signal paths including the bio-impedance and two branch impedances.

In Example 7, the method of any one of Examples 1-6 can optionally include each unique signal path includes a network of all of the impedances.

Example 8 is a circuit for measuring impedances, comprising: a signal generator to generate a signal at an output of the signal generator, current measurement circuitry to measure a current at an input of the current measurement circuitry, a configurable network to connect the output of the signal generator to the input of the current measurement circuitry through unique signal paths, wherein each unique signal path includes at least some of: a bio-impedance and branch impedances, and digital circuitry to determine the bio-impedance and the branch impedances based on current measurements of the unique signal paths.

In Example 9, the circuit of Example 8 can optionally include: the configurable network being to connect the output of the signal generator to the input of the current measurement circuitry through at least five unique signal paths, and the current measurement circuitry being to measure at least five current measurements.

In Example 10, the circuit of Example 8 or 9 can optionally include the digital circuitry being to determine the bio-impedance and four branch impedances based on the at least five current measurements of the unique signal paths.

In Example 11, the circuit of any one of Examples 8-10 can optionally include the unique signal paths including each one of the bio-impedance and branch impedances at least once.

In Example 12, the circuit of any one of Examples 8-11 can optionally include each unique signal path including two branch impedances.

In Example 13, the circuit of any one of Examples 8-12 can optionally include each one of some of the unique signal paths including the bio-impedance and two branch impedances.

In Example 14, the circuit of any one of Examples 8-13 can optionally include each unique signal path including a network of all of the bio-impedance and the branch impedances.

In Example 15, the circuit of any one of Examples 8-14 can optionally include the configurable network being to further connect the output of the signal generator to the input of the current measurement circuitry through a resistor with a known resistance value, and the current measurement circuitry being to further measure a current through the resistor to determine a voltage from the signal generator.

Example 16 is a circuit for measuring impedances, comprising: four branches having four electrodes respectively, wherein two of the four electrodes are connected to a first end of a bio-impedance, and two other ones of the four electrodes are connected to a second end of the bio-impedance, circuitry to apply a signal to at least five unique impedance networks and making current measurements of the at least five unique impedance networks, wherein each unique impedance network has at least two of the four branches, digital circuitry to derive the bio-impedance and impedances of the four branches based on the current measurements.

In Example 17, the circuit of Example 16 can optionally include each unique impedance network including all of the four branches.

In Example 18, the circuit of Example 16 or 17 can optionally include the at least five unique impedance networks comprising a unique impedance network having one of the four branches connected to a signal generator and three other ones of the four branches connected to current measurement circuitry.

In Example 19, the circuit of any one of Examples 16-18 can optionally include the at least five unique impedance networks comprising a second unique impedance network having two of the four branches connected to a signal generator and two other ones of the four branches connected to current measurement circuitry.

In Example 20, the circuit of any one of Examples 16-19 can optionally include the circuitry being to further connect an output of a signal generator to an input of current measurement circuitry through a resistor with known resistance value and to further measure a current through the resistor to determine a measured voltage from the signal generator.

In Example 21, the circuit of any one of Examples 16-20 can optionally include the digital circuitry being to determine quality of contacts corresponding to the four electrodes based on the impedances of the four branches.

In Example 22, the circuit of any one of Examples 16-21 can optionally include the unique impedance networks including each one of the bio-impedance and impedances of the four branches at least once.

In Example 23, the circuit of any one of Examples 16-22 can optionally include each one of some of the unique impedance networks includes the bio-impedance and impedances of two of the four branches.

In Example 24, the circuit of any one of Examples 16-23 can optionally include each unique impedance networks includes a network of all of the bio-impedance and impedances of the four branches.

Variations and Implementations

The unique signal paths illustrated by the disclosure are not meant to be limiting. Other topologies, schemes for exciting and measuring the signal paths can be implemented, and are envisioned by the disclosure.

Moreover, certain embodiments discussed above can be provisioned in digital signal processing technologies for medical imaging, patient monitoring, medical instrumentation, and home healthcare. The embodiments herein can also be beneficial to other applications requiring an accurate impedance measurement using at least four electrodes.

In the discussions of the embodiments above, various electrical components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure.

Parts of various circuitry for deriving unknown impedances can include electronic circuitry to perform the functions described herein. In some cases, one or more parts of the circuitry can be provided by a processor specially configured for carrying out the functions described herein. For instance, the processor may include one or more application specific components, or may include programmable logic gates which are configured to carry out the functions describe herein. The circuitry can operate in analog domain, digital domain, or in a mixed signal domain. In some instances, the processor may be configured to carrying out the functions described herein by executing one or more instructions stored on a non-transitory computer medium. In some embodiments, an apparatus can include means for performing or implementing one or more of the functionalities describe herein.

It is also imperative to note that all of the specifications, dimensions, and relationships outlined herein (e.g., the number of processors, logic operations, etc.) have only been offered for purposes of example and teaching only. Such information may be varied considerably without departing from the spirit of the present disclosure. The specifications apply only to one non-limiting example and, accordingly, they should be construed as such. In the foregoing description, example embodiments have been described with reference to particular processor and/or component arrangements. Various modifications and changes may be made to such embodiments without departing from the scope of the disclosure. The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to deriving unknown impedances, illustrate only some of the possible functions that may be executed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure.

What is claimed is:

1. A circuit for measuring impedances, comprising:
a signal generator to generate a signal at an output of the signal generator,
measurement circuitry to make measurements at an input of the measurement circuitry,
a configurable network to couple the output of the signal generator to the input of the measurement circuitry through at least five unique signal paths, wherein each unique signal path forms a network having an impedance of interest and four branch impedances, and
digital circuitry to determine the impedance of interest and the four branch impedances based on at least five measurements of the unique signal paths made by the measurement circuitry and a calibration measurement of the signal generator.

2. The circuit of claim 1, wherein one of the unique signal paths includes two of the branch impedances coupled in parallel.

3. The circuit of claim 1, wherein one of the unique signal paths includes two of the branch impedances coupled in parallel with each other, and the two branch impedances coupled in parallel are in series with the impedance of interest.

4. The circuit of claim 1, wherein:
a first one and a second one of the four branch impedances are coupled to a first end of the impedance of interest,
a third one and a fourth one of the four branch impedances are coupled to a second end of the impedance of interest, and
for one of the unique signal paths:
the first one of the four branch impedances is coupled to the output of the signal generator, and
the second one, the third one, and the fourth one of the four branch impedances are coupled to the input of the measurement circuitry.

5. The circuit of claim 1, wherein:
a first one and a second one of the four branch impedances are coupled to a first end of the impedance of interest,
a third one and a fourth one of the four branch impedances are coupled to a second end of the impedance of interest, and
for one of the unique signal paths:
the second one of the four branch impedances is coupled to the output of the signal generator, and
the first one, the third one, and the fourth one of the four branch impedances are coupled to the input of the measurement circuitry.

6. The circuit of claim 1, wherein:
a first one and a second one of the four branch impedances are coupled to a first end of the impedance of interest,
a third one and a fourth one of the four branch impedances are coupled to a second end of the impedance of interest, and
for one of the unique signal paths:
the third one of the four branch impedances is coupled to the output of the signal generator, and
the first one, the second one, and the fourth one of the four branch impedances are coupled to the input of the measurement circuitry.

7. The circuit of claim 1, wherein:
a first one and a second one of the four branch impedances are coupled to a first end of the impedance of interest,
a third one and a fourth one of the four branch impedances are coupled to a second end of the impedance of interest, and
for one of the unique signal paths:
the fourth one of the four branch impedances is coupled to the output of the signal generator, and
the first one, the second one, and the third one of the four branch impedances are coupled to the input of the measurement circuitry.

8. The circuit of claim 1, wherein:
a first one and a second one of the four branch impedances are coupled to a first end of the impedance of interest,
a third one and a fourth one of the four branch impedances are coupled to a second end of the impedance of interest, and
for one of the unique signal paths:
the first one and the second one of the four branch impedances are coupled to the output of the signal generator, and
the third one and the fourth one of the four branch impedances are coupled to the input of the measurement circuitry.

9. An integrated circuit for measuring impedances, comprising:
first and second pins electrically couplable to a first end of an impedance of interest,
third and fourth pins electrically couplable to a second end of the impedance of interest,
a signal generator to generate a signal at an output of the signal generator,
measurement circuitry to make measurements at an input of the measurement circuitry,
a configurable network to electrically couple each one the first, second, third, and fourth pins to either the output of the signal generator or the input of the measurement circuit to form at least five unique closed circuits each having the first, second, third, and fourth pins and the impedance of interest, and
digital circuitry to determine four branch impedances associated with the first, second, third, and fourth pins, and the impedance of interest based on at least five measurements of the unique closed circuits made by the measurement circuitry and a calibration measurement of the signal generator.

10. The integrated circuit of claim 9, wherein one of the unique closed circuits includes two of the branch impedances coupled in parallel.

11. The integrated circuit of claim 9, wherein one of the unique closed circuits includes two of the branch impedances coupled in parallel with each other, and the two branch impedances coupled in parallel are in series with the impedance of interest.

12. The integrated circuit of claim 9, wherein for one of the unique closed circuits,
the first pin is electrically coupled to the output of the signal generator, and
the second pin, the third pin, and the fourth pin are electrically coupled to the input of the measurement circuitry.

13. The integrated circuit of claim 9, wherein for one of the unique closed circuits,
the second pin is electrically coupled to the output of the signal generator, and
the first pin, the third pin, and the fourth pin are electrically coupled to the input of the measurement circuitry.

14. The integrated circuit of claim 9, wherein for one of the unique closed circuits,
the third pin is electrically coupled to the output of the signal generator, and
the first pin, the second pin, and the fourth pin are electrically coupled to the input of the measurement circuitry.

15. The integrated circuit of claim 9, wherein for one of the unique closed circuits,
the fourth pin is electrically coupled to the output of the signal generator, and
the first pin, the second pin, and the third pin are electrically coupled to the input of the measurement circuitry.

16. The integrated circuit of claim 9, wherein for one of the unique closed circuits,
the first pin and the second pin are electrically coupled to the output of the signal generator, and
the third pin, and the fourth pin are electrically coupled to the input of the measurement circuitry.

17. A method for measuring impedances, the impedances including an impedance of interest and four branch impedances, comprising:
forming five unique signal paths having all impedances, wherein forming each unique signal path comprises: (1) coupling a signal generator to a subset of four branches, and (2) coupling remaining branches not in the subset of four branches to measurement circuitry,
making five measurements of the unique signal paths by the measurement circuitry, wherein making each measurement comprises: (1) applying a signal to the subset of the four branches coupled to the signal generator, and (2) making a measurement of the remaining branches coupled to the measurement circuitry, and
deriving the impedances based on the five measurements.

18. The method of claim 17, wherein forming the five unique signal paths comprises controlling a configurable network to couple each branch to either the signal generator or the measurement circuitry, the signal generator being coupled to at least one branch, the measurement circuitry being coupled to at least two branches.

19. The method of claim 17, wherein forming the five unique signal paths does not include grounding any one of the four branches.

20. The method of claim 17, wherein deriving the impedances is further based on a calibration measurement of the signal generator.

* * * * *